(12) United States Patent
Gonzalez et al.

(10) Patent No.: US 10,342,522 B2
(45) Date of Patent: Jul. 9, 2019

(54) SYSTEMS AND METHODS FOR TREATING FISTULAS IN THE LUNG AND TRACHEA

(71) Applicant: SPIRATION, INC., Redmond, WA (US)

(72) Inventors: Hugo Xavier Gonzalez, Woodinville, WA (US); William A. Sirokman, Kirkland, WA (US); Brandon Shuman, Kirkland, WA (US); Richard Shea, Kenmore, WA (US); David Dillard, Grapeview, WA (US)

(73) Assignee: Spiration, Inc., Redmond, WA (US)

( * ) Notice: Subject to any disclaimer, the term of this patent is extended or adjusted under 35 U.S.C. 154(b) by 507 days.

(21) Appl. No.: 14/332,027

(22) Filed: Jul. 15, 2014

(65) Prior Publication Data

US 2014/0330309 A1 Nov. 6, 2014

Related U.S. Application Data

(63) Continuation of application No. PCT/US2012/071832, filed on Dec. 27, 2012.
(Continued)

(51) Int. Cl.
*A61B 17/03* (2006.01)
*A61B 17/00* (2006.01)
*A61B 17/12* (2006.01)

(52) U.S. Cl.
CPC ...... *A61B 17/0057* (2013.01); *A61B 17/1215* (2013.01); *A61B 17/12104* (2013.01);
(Continued)

(58) Field of Classification Search
CPC ........ A61L 31/06; A61L 31/16; A61L 31/148; A61L 31/14; A61L 2300/216;
(Continued)

(56) References Cited

U.S. PATENT DOCUMENTS 5,370,657 A * 12/1994 Irie ........................... A61F 2/01
606/200
6,231,589 B1 * 5/2001 Wessman ................... A61F 2/01
606/200
(Continued)

FOREIGN PATENT DOCUMENTS

DE 233303 A1 12/1990
DE 11 2012 005 689 T5 10/2014
(Continued)

OTHER PUBLICATIONS

International, PCT Search Report and Written Opinion, dated May 17, 2013, re PCT Application No. PCT/US12/71832.
(Continued)

*Primary Examiner* — Kari K Rodriquez
*Assistant Examiner* — Camtu T Nguyen

(57) ABSTRACT

In certain embodiments, a device is configured to be compressed and inserted into the distal end of an endoscope. The delivery device can be configured to deliver the delivery catheter to the site of one or more fistulas in the wall of a body cavity or lumen within a patient. The delivery catheter is configured to deliver the device to the site of the one or more fistulas. The device is configured to expand at the site of the one or more fistulas and substantially seal the fistula in one or more directions. In some embodiments, at least a portion of the device is coated with and/or constructed of biocompatible material. In some configurations, the device is configured to be implanted for an extended period of time or even permanently. In some embodiments, at least a portion of the device is constructed of biodegradable, dissolvable and/or bioabsorbable material.

4 Claims, 26 Drawing Sheets

Related U.S. Application Data

(60) Provisional application No. 61/587,621, filed on Jan. 17, 2012.

(52) U.S. Cl.
CPC .. *A61B 17/12145* (2013.01); *A61B 17/12159* (2013.01); *A61B 17/12172* (2013.01); *A61B 17/12177* (2013.01); *A61B 2017/00575* (2013.01); *A61B 2017/00579* (2013.01); *A61B 2017/00584* (2013.01); *A61B 2017/00588* (2013.01); *A61B 2017/00592* (2013.01); *A61B 2017/00597* (2013.01); *A61B 2017/00606* (2013.01); *A61B 2017/00619* (2013.01); *A61B 2017/00623* (2013.01)

(58) Field of Classification Search
CPC ......... A61L 2300/252; A61L 2300/254; A61L 31/005; A61L 31/046; A61L 2430/036; A61L 2300/606; A61L 24/001; A61L 24/0042; A61F 6/20; A61F 6/22; A61F 6/225; A61F 2/01; A61F 2002/016; A61F 2230/008; A61B 17/0057; A61B 17/12159; A61B 17/12145; A61B 17/1215; A61B 17/12099; A61B 17/12104; A61B 17/12172; A61B 17/12177; A61B 2017/00575; A61B 2017/00579; A61B 2017/00584; A61B 2017/005; A61B 2017/00588; A61B 17/12022; A61B 17/12027; A61B 17/12031; A61B 17/12036; A61B 17/1204; A61B 17/12045; A61B 17/12109; A61B 2230/008; A61B 2017/00597; A61B 2017/00601; A61B 2017/00606; A61B 2018/0038; A61B 2017/00; A61M 29/02
USPC .............................. 606/191, 213; 128/200.24
See application file for complete search history.

(56) References Cited

U.S. PATENT DOCUMENTS

| | | | |
|---|---|---|---|
| 6,652,556 B1 | 11/2003 | Van Tassel | |
| 6,997,918 B2* | 2/2006 | Soltesz | A61B 17/12022 128/200.24 |
| 7,011,094 B2* | 3/2006 | Rapacki | A61B 17/12022 128/200.24 |
| 7,195,636 B2* | 3/2007 | Avellanet | A61B 17/12022 606/151 |
| 7,323,005 B2 | 1/2008 | Wallace | |
| 7,533,671 B2 | 5/2009 | Gonzalez et al. | |
| 2007/0005083 A1 | 1/2007 | Sabanathan | |
| 2007/0088381 A1* | 4/2007 | McGuckin, Jr. | A61F 2/01 606/200 |
| 2007/0088383 A1* | 4/2007 | Pal | A61F 2/013 606/200 |
| 2007/0129757 A1 | 6/2007 | Armstrong | |
| 2007/0265658 A1* | 11/2007 | Nelson | A61B 17/00234 606/213 |
| 2010/0249828 A1* | 9/2010 | Mavani | A61B 17/0057 606/213 |
| 2011/0208228 A1* | 8/2011 | Gonzalez | A61B 17/12022 606/191 |

FOREIGN PATENT DOCUMENTS

| | | |
|---|---|---|
| GB | 2513068 | 10/2014 |
| JP | 02307480 A | 2/1986 |
| WO | WO 2007/033379 | 3/2007 |
| WO | WO 2007/115208 | 10/2007 |
| WO | WO 2013/109398 | 7/2013 |

OTHER PUBLICATIONS

International, PCT International Preliminary Report on Patentability, dated Jul. 22, 2014, re PCT Application No. PCT/US12/71832.

* cited by examiner

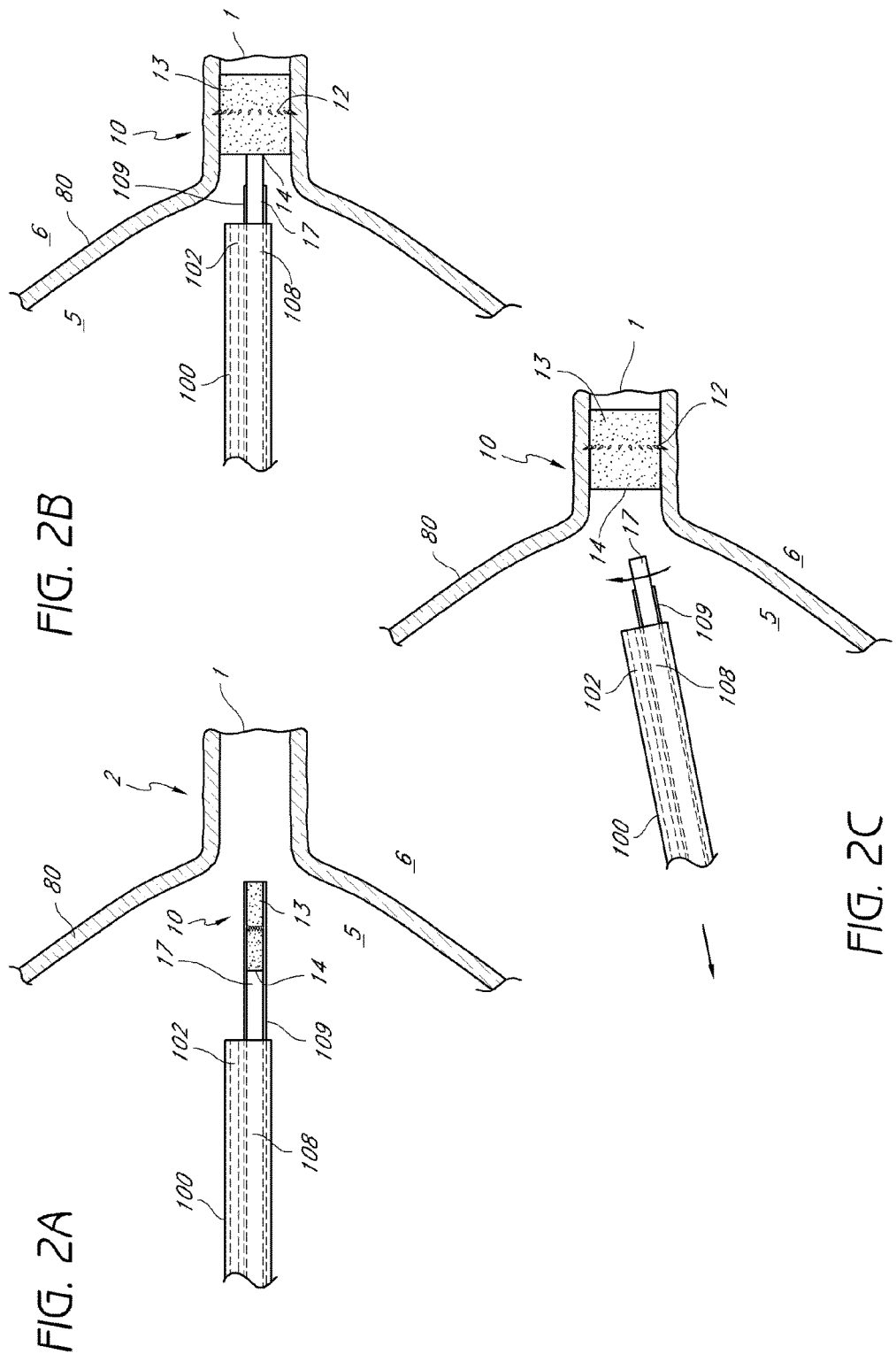

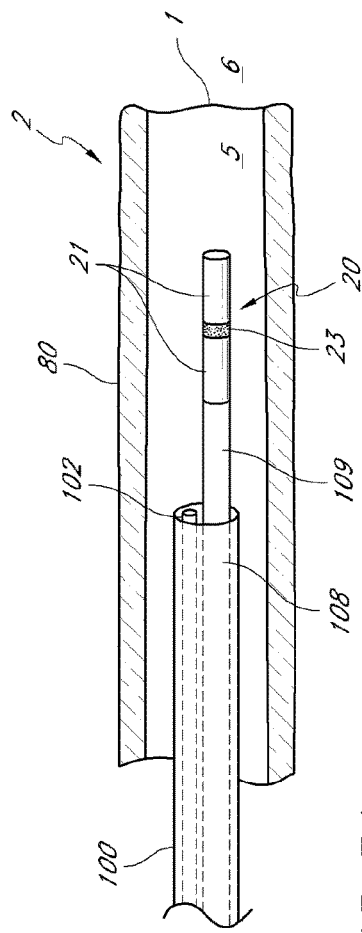
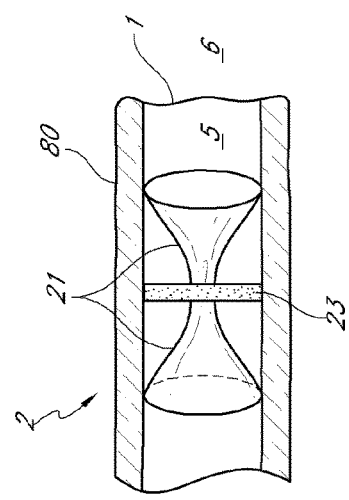
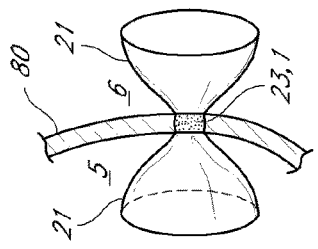
FIG. 3A
FIG. 3B
FIG. 3C

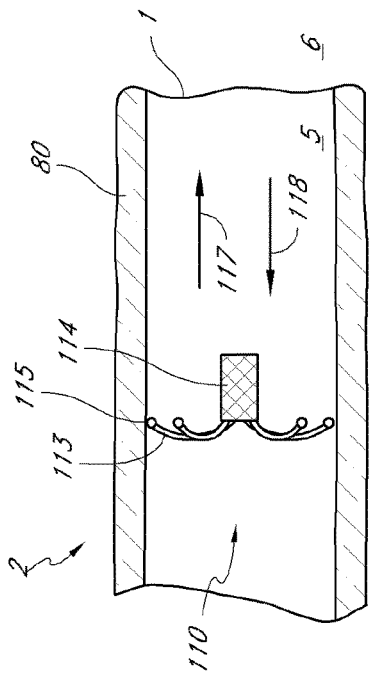
FIG. 7B
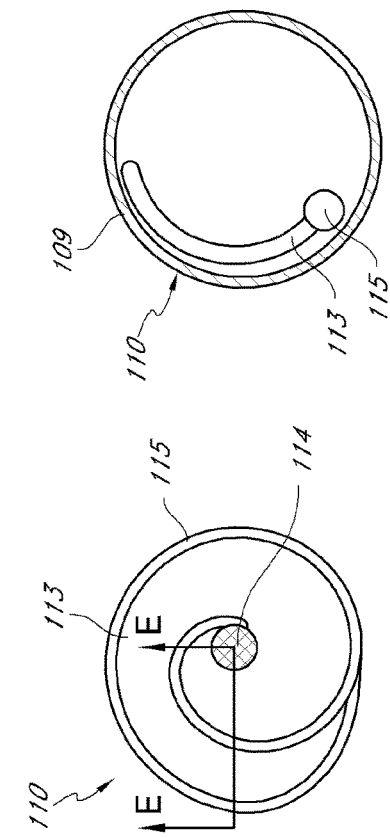
FIG. 7A
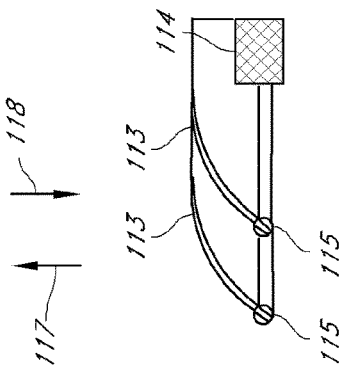
FIG. 7C
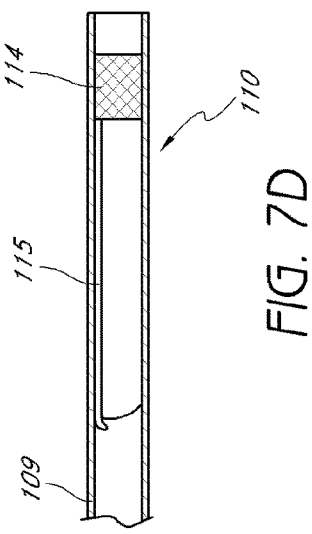
FIG. 7E
FIG. 7D

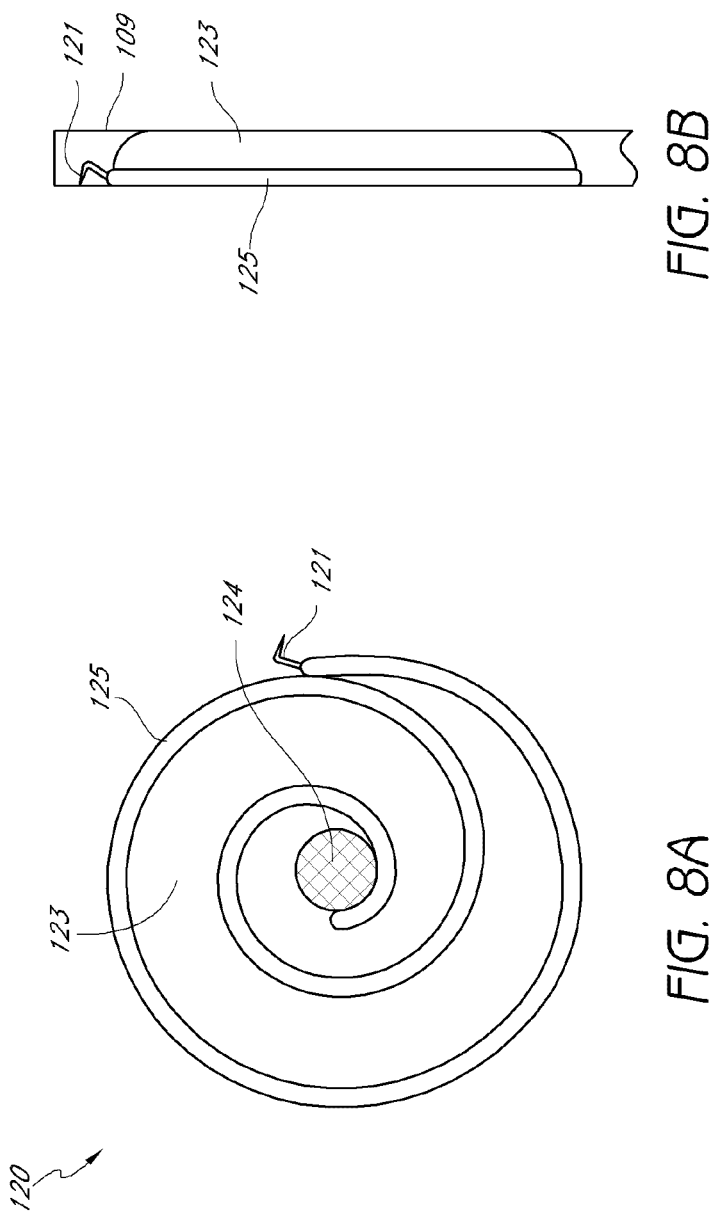

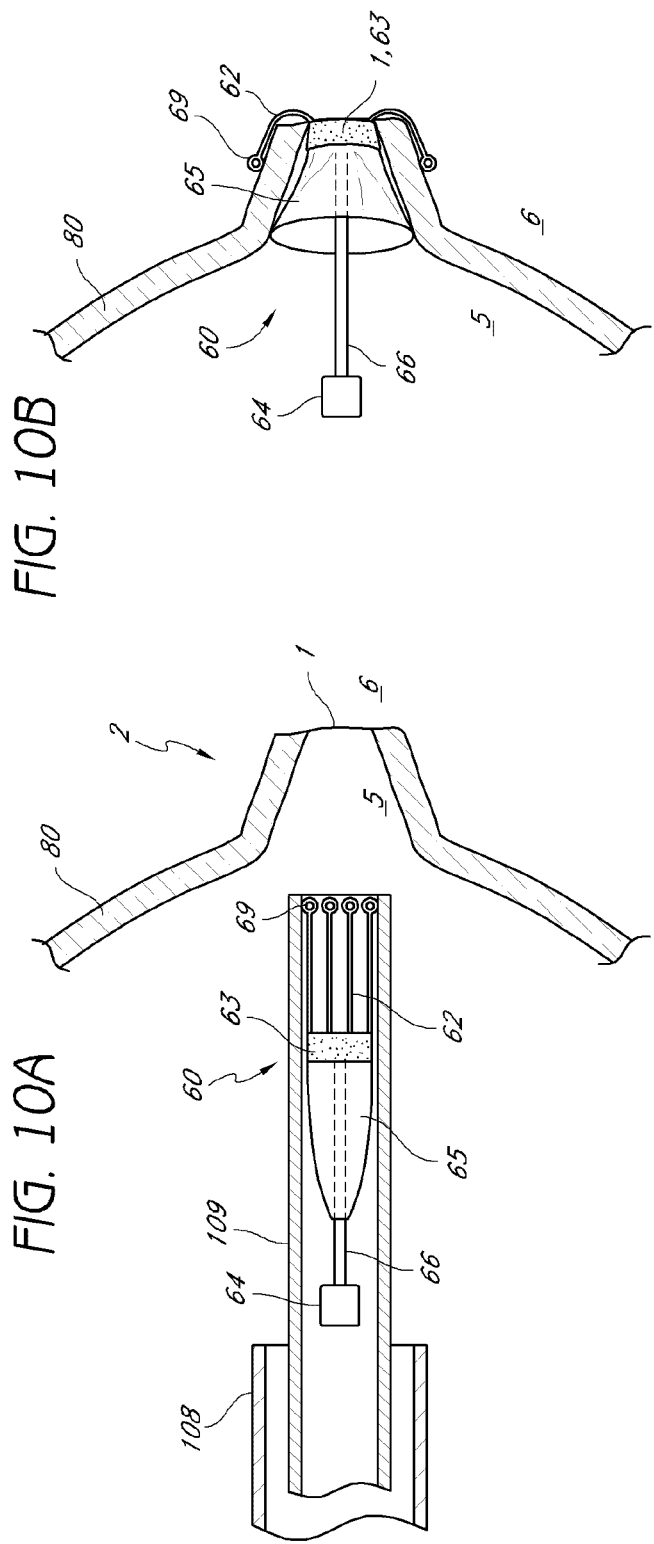

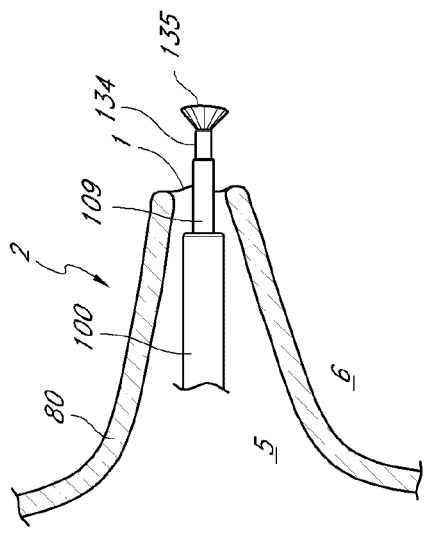
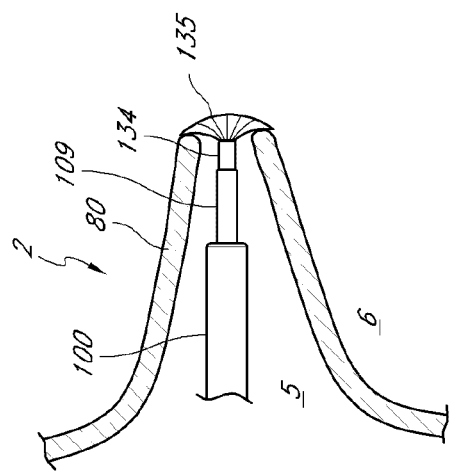
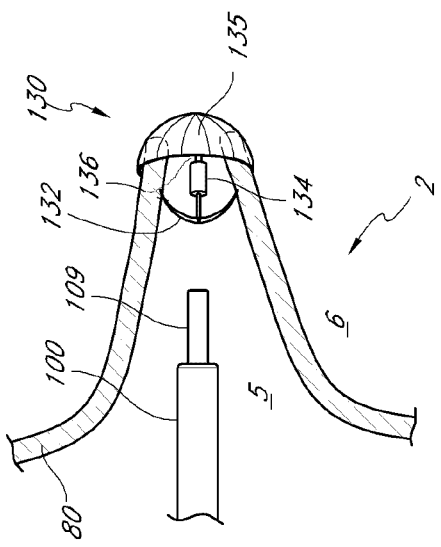
FIG. 12A
FIG. 12B
FIG. 12C

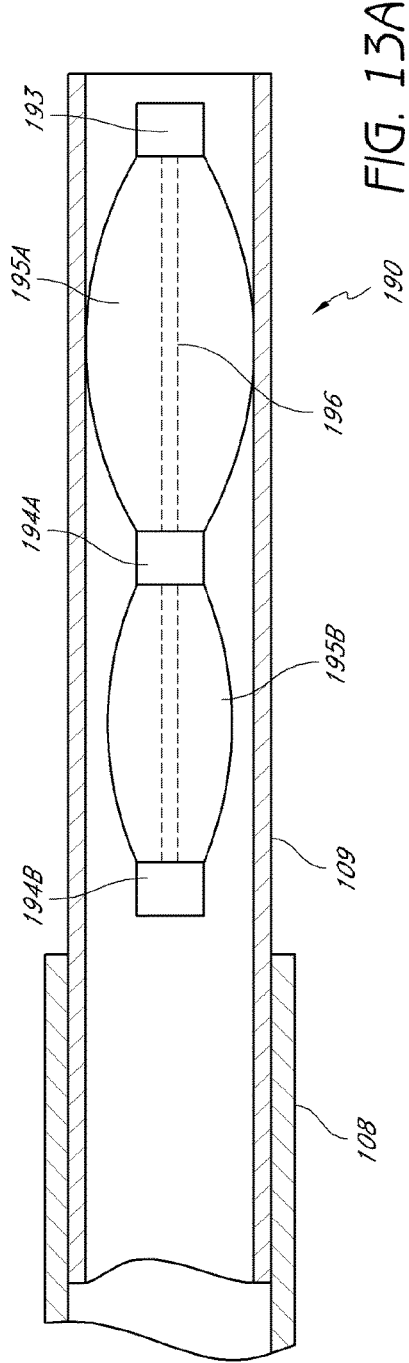

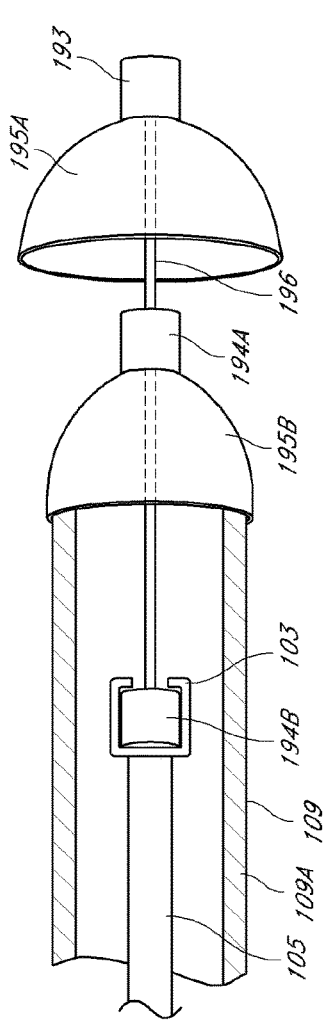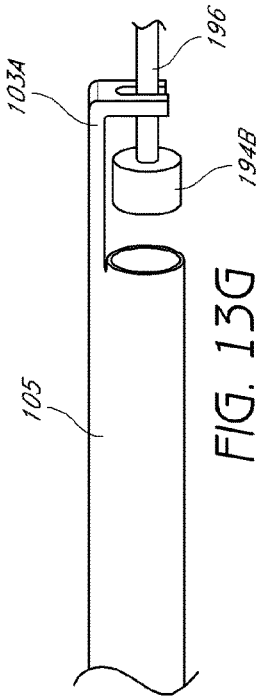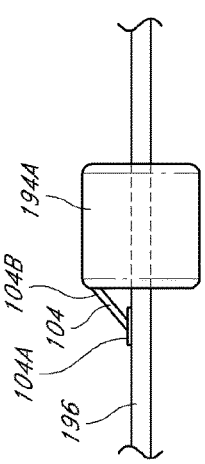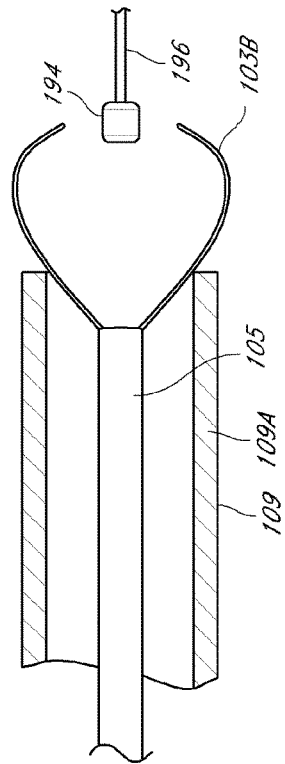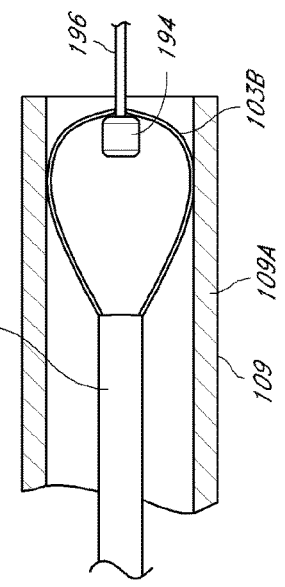

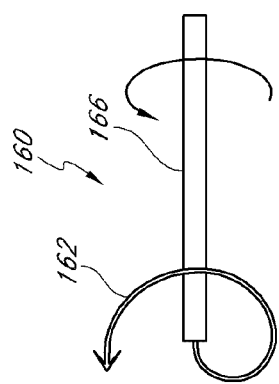
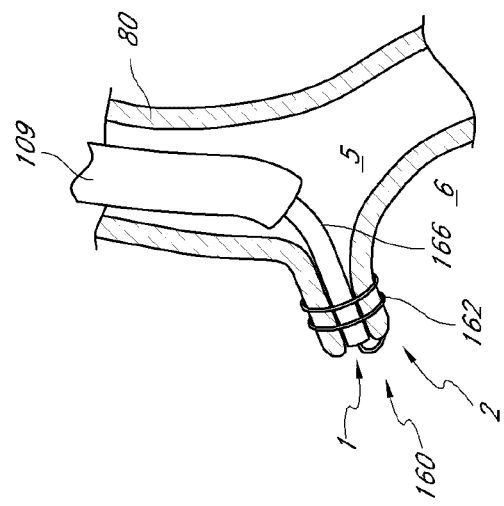
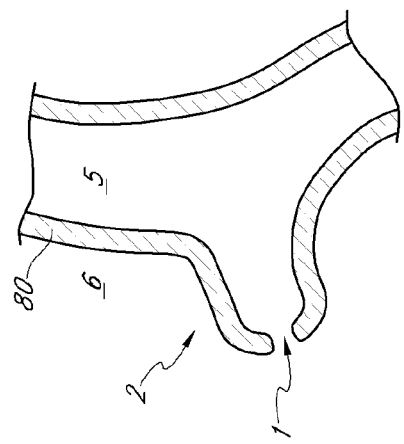
FIG. 14A
FIG. 14B
FIG. 14C

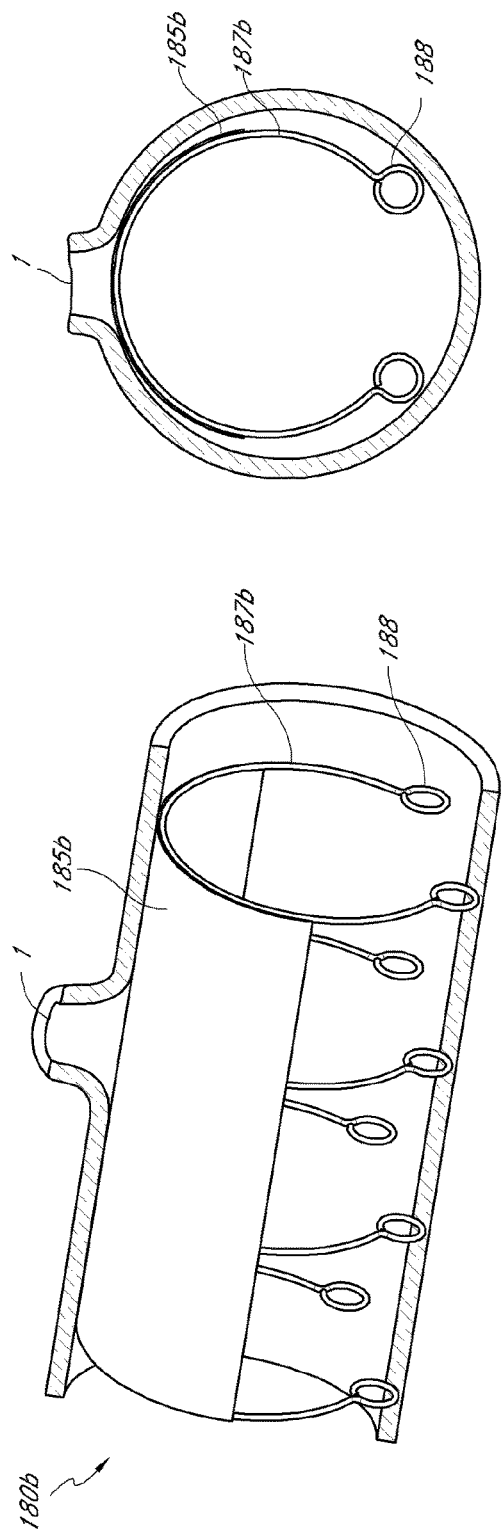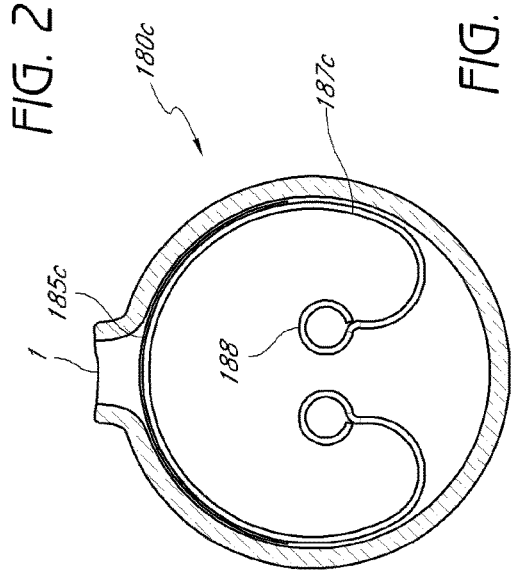
FIG. 21A
FIG. 21B
FIG. 22

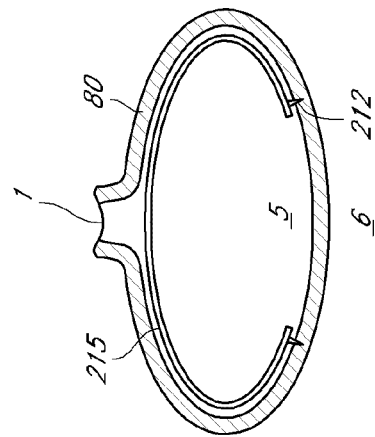
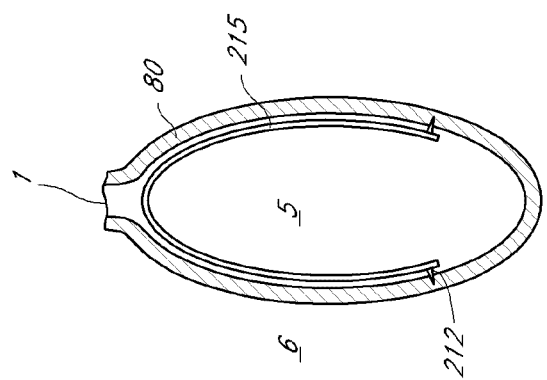
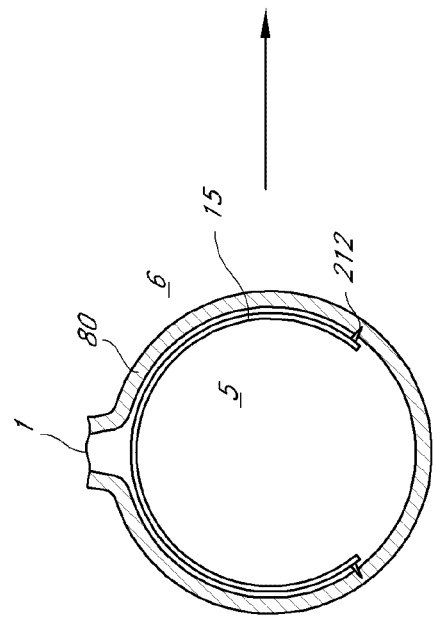
FIG. 23D
FIG. 23E

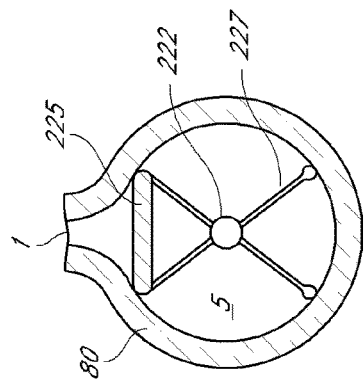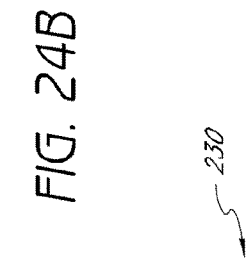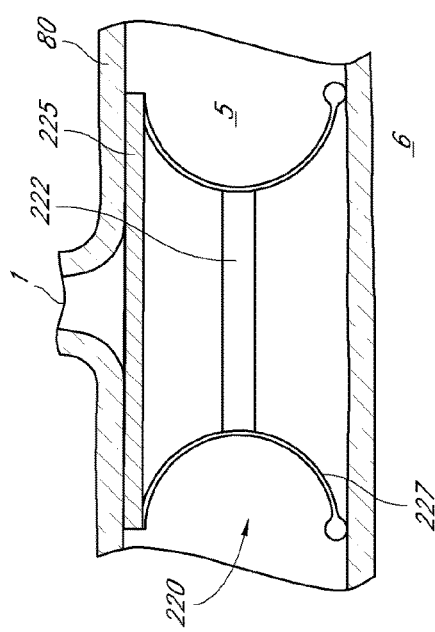

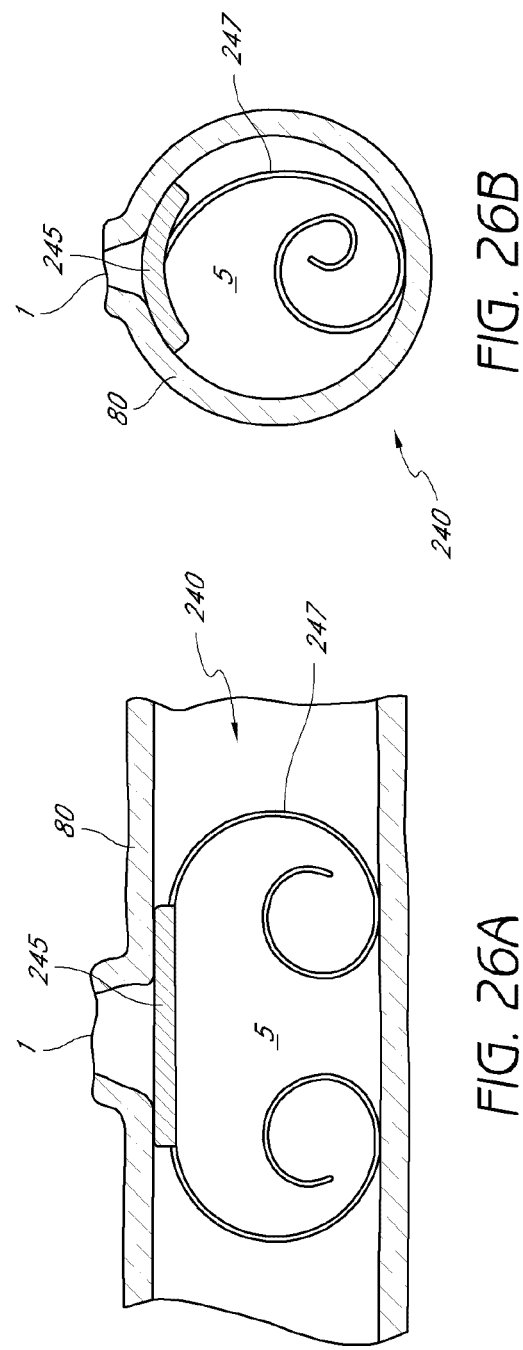

SYSTEMS AND METHODS FOR TREATING FISTULAS IN THE LUNG AND TRACHEA

RELATED APPLICATIONS

Any and all priority claims identified in the Application Data Sheet, or any correction thereto, are hereby incorporated by reference under 37 CFR 1.57.

BACKGROUND OF THE INVENTION

Field of the Invention

The present invention relates in general to the field of pulmonary treatments, and specifically to methods of sealing fistulas and ruptures in a lung or trachea.

Description of the Related Art

Described herein are systems and methods for sealing an airway rupture or fistula to stop, reduce, and/or control leaks of lung airways that have been damaged or have a defect. Also disclosed are systems and methods for controlling a transfer of a fluid, gas and/or liquid between two spaces. One common clinical condition in which such transfer can occur is called a "stump leak" fistula.

A stump is the remnant of an airway that has been resected as close as possible to its anatomical origin. Stump leaks can occur after a surgery has been performed to remove a lobe (lobectomy) or a whole lung (pneumonectomy). During surgery, the lung tissue is resected, as well as the airways and blood vessels that feed that portion of lung tissue. Therefore, during the resection, the surgeon will attempt to cut the tissue as close as possible to its anatomical origin.

After resection, stump leaks may occur because it is sometimes difficult to cut and completely seal the large diameter airways. Another cause of a stump leak could be the dehiscence of sutures that were keeping the airway(s) closed. As a consequence, in the post-surgical phase, the defect will produce leakage of air and/or fluid into the thoracic cavity. Another cause of stump leak could be an infection in the vicinity of a sutured airway. Such an infection could degrade the tissue surrounding the suture and cause stump leaks and other fistulas to form.

Some solutions have been developed for the treatment of fistulas and ruptures of the lung and/or trachea. For example, treatment methods such as pleurodesis, the use of lasers, cryoablation, cauterization and/or the placement of packing materials into the fistula/rupture have been used. Some of these solutions, however, have significant drawbacks. For example, pleurodesis may not work in the context of pneumonectomies because there is no lung pleura to attach to the chest wall pleura. Due to the inherent limitations of many of the above treatment methods and devices, there remains a need for improvement to devices and methods for the treatment of airway fistulas and/or ruptures.

SUMMARY OF THE INVENTION

A system for repairing fistulas and/or ruptures in airways can comprise solid plugs, conical plugs, spiral plugs, hollow cylindrical plugs, and/or other devices configured to be delivered to the site of the fistula/rupture via a delivery device that can extend through a working channel in a bronchoscope, endoscope or other such apparatus.

The devices and methods disclosed herein are generally aimed at the sealing and/or blocking of fistulas within a patient. Some of the devices and methods are designed to allow or control fluid flow through the fistula in at least one direction. Other devices are designed to block all fluid flow through the fistula, thereby sealing the interior of body tissue and/or organs from surrounding cavities and/or other organs. Some embodiments of the devices disclosed are configured to be single plane—e.g., designed to block/seal a fistula from one side. Other embodiments of the devices disclosed are configured to be multi-planar—e.g., designed to block/seal a fistula from both sides.

In some embodiments, a device for treating fistulas in walls of a body cavity includes one or more frame members. The one or more frame members can be configured to transition between a compressed configuration and an expanded configuration. The one or more frame members can be configured to form a tube with a substantially cylindrical shape that fits within a body lumen when the one or more frame members are in an expanded configuration. The one or more frame members can be configured to fit within a working channel of an endoscope when the one or more frame members are in a compressed configuration.

In some configurations, a device for treating fistulas in walls of a body cavity or lumen is configured to transition between a compressed configuration and an expanded configuration. The device can further be configured to fit within the working channel of an endoscope when the device is in a compressed configuration. The device can include one or more frame members that are configured to transition between a compressed configuration and an expanded configuration. The frame members can be configured to form a tube with a substantially c-shaped cross-section when the frame members are in an expanded configuration. In some embodiments, the frame members are configured to fit within a working channel of an endoscope when the frame members are in a compressed configuration.

In some embodiments, a device for treating fistulas in walls of a body cavity or lumen is configured to transition between a compressed configuration and an expanded configuration. The device can further be configured to fit within the working channel of an endoscope when the device is in a compressed configuration. The device can include one or more inflatable portions configured to transition between a deflated and an inflated configuration. The inflatable portions can be configured to restrict the flow of fluid through a fistula in at least one direction when the inflatable portions are in an inflated configuration and deployed at the site of a fistula. The device can also include one or more inflation points on the inflatable portions configured to facilitate fluid communication between the inflatable portions and one or more sources of inflating substance. In some embodiments, the device includes one or more stabilizing members connected to the inflatable portions and configured to inhibit movement of the inflatable portions when the inflatable portions are in an inflated configuration and deployed within the body of a patient.

According to some embodiments, a device for treating fistulas in walls of a body cavity or lumen is configured to transition between a compressed configuration and an expanded configuration. The device can further be configured to fit within the working channel of an endoscope when the device is in a compressed configuration. The device can include one or more conical portions configured to transition between a compressed and an expanded configuration. The conical portions can be configured to restrict the flow of fluid through a fistula in at least one direction when the conical portions are in an expanded configuration and deployed at the site of a fistula. Furthermore, the device can include one or more hub portions, each having a first end and a second end. The hub portions can be configured to connect to at least one of the conical portions.

In some embodiments, a device for treating fistulas in walls of a body cavity or lumen is configured to transition between a compressed configuration and an expanded configuration. The device can further be configured to fit within the working channel of an endoscope when the device is in a compressed configuration. The device can include one or more spiral portions configured to transition between a compressed and an expanded configuration. The spiral portions can be configured to restrict the flow of fluid through a fistula in at least one direction when the spiral portions are in an expanded configuration and deployed at the site of a fistula. The device can also include one or more hub portions, each comprising a first end and a second end. The hub portions can be configured to connect to at least one of the spiral portions.

A method of delivering a treatment device for treating fistulas in the walls of a body cavity or lumen to the body cavity or lumen can include providing the treatment device and then compressing the treatment device. The method could include then loading the treatment device into the distal end of a delivery device then positioning the distal end of the delivery device near the site of one or more fistulas. The treatment device can then be removed from the distal end of the delivery device and expanded such that the treatment device inhibits fluid flow through the one or more fistulas in at least one direction.

Additionally, some embodiments of the devices disclosed herein are designed to be long-term or even permanent implantations. Such embodiments could be constructed of biocompatible materials such that the tissue surrounding the device could grow into or onto the device. Additionally or alternatively, some of the embodiments disclosed herein are designed to be removable. Removable devices could be designed to block/seal a fistula for a long enough time to allow the patient's body to heal the fistula or rupture. After the fistula or rupture has healed, the removable device could be removed from the patient's body.

BRIEF DESCRIPTION OF THE DRAWINGS

Various embodiments are depicted in the accompanying drawings for illustrative purposes, and should in no way be interpreted as limiting the scope of the embodiments. In addition, various features of different disclosed embodiments can be combined to form additional embodiments, which are part of this disclosure.

FIG. 2A is a side view of an embodiment of a plug device and an inflation device within a delivery catheter, as well as an extended fistula in the wall of a body lumen or cavity.

FIG. 2B is an side view of the plug and catheter of FIG. 2A, with the plug in an inflated configuration.

FIG. 2C is a side view of the inflated plug of FIG. 2B, with the inflation device disconnected from the plug.

FIG. 3A is a perspective view of an embodiment of a double cone valve within a delivery catheter.

FIG. 3B is a perspective view of the double cone valve of FIG. 3A deployed in a stump.

FIG. 3C is a perspective view of the double cone valve of FIG. 3A deployed in a fistula in the side wall of a body lumen or cavity.

FIG. 7A is a front view of an embodiment of a spiral flap valve in an unfurled configuration.

FIG. 7B is a front view of the spiral flap valve of FIG. 7A in a compressed configuration within a delivery catheter.

FIG. 7C is a side cross-sectional view of the spiral flap valve of FIG. 7A deployed in a stump.

FIG. 7D is side view of the spiral flap valve of FIG. 7A compressed within a delivery catheter.

FIG. 7E is a cross-section view of the spiral flap valve of FIG. 7A along the viewing-plain E-E in FIG. 7A.

FIG. 8A is a front view of an embodiment of a spiral valve with an end barb in an unfurled configuration.

FIG. 8B is a side view of the spiral valve of 8A compressed within a delivery catheter.

FIG. 10A is a side view of an embodiment of a cone valve with anchors having atraumatic ends, the cone valve compressed within a delivery catheter.

FIG. 10B is a perspective view of the cone valve of FIG. 10A deployed in a stump.

FIG. 12A is a side view of an embodiment of a cone valve partially removed from a delivery catheter at the site of a stump.

FIG. 12B is a side view of the cone valve of FIG. 12A further removed from a delivery catheter as the site of a stump.

FIG. 12C is a side view of the cone valve of FIG. 12A deployed on and in a stump.

FIG. 13A is a side view of an embodiment of a double cone valve compressed within a delivery catheter.

FIG. 13B is a perspective view of the double cone valve of FIG. 13A with one of the cones removed from a delivery catheter outside a stump.

FIG. 13C is a perspective view of the double cone valve of FIG. 13A with both cones removed from the delivery catheter at the site of a stump.

FIG. 13D is a perspective view of the double cone valve of FIG. 13A, deployed at the site of a stump.

FIG. 13E is a perspective view of the double cone valve of FIG. 13A and an embodiment of a push-pull mechanism.

FIG. 13F is a side view of a ratchet mechanism of the double cone valve of FIG. 13A.

FIG. 13G is a perspective view of an embodiment of the push-pull mechanism of FIG. 13E, the push-pull mechanism having a hook.

FIG. 13H is a side view of an embodiment of the push-pull mechanism of FIG. 13E within a delivery catheter, the push-pull mechanism having a plurality of fingers.

FIG. 13I is a side view of the push-pull mechanism of FIG. 13F partially outside of a catheter.

FIG. 14A is a side view of an embodiment of a barbed anchor.

FIG. 14B is a side cross-section view of a tapered stump.

FIG. 14C is a side view of the barbed anchor of FIG. 14A and tapered stump of FIG. 14B, the tapered stump sealed by the barbed anchor.

FIG. 21A is a perspective view of an embodiment of a partially-covered hollow cylinder deployed in a body lumen.

FIG. 21B is a front view of the partially-covered hollow cylinder of FIG. 21A.

FIG. 22 is a front view of an embodiment of a partially-covered hollow cylinder deployed in a body lumen.

FIG. 23D is a front view of the ring device of FIG. 23A deployed in a body lumen.

FIG. 23E is a front view of the ring device of FIG. 23A in two partially-collapsed body lumens.

FIG. 24A is a side cross-section view of an embodiment of an x-frame plug in a body lumen.

FIG. 24B is a front cross-section view of the x-frame plug of FIG. 24A.

FIG. 25 is a perspective view of an embodiment of a jellyfish plug.

FIG. 26A is a side cross-section view of an embodiment of a bench plug in a body lumen.

FIG. 26B is a front view of the bench plug of FIG. 26A.

DETAILED DESCRIPTION OF THE PREFERRED EMBODIMENT

The methods, systems, and devices described herein involve minimally invasive procedures for treating fistulas and/or ruptures in body tissue and organs, for example airways or lung bronchi. Although portions of the following description are provided with reference to fistulas/ruptures caused during thoracic surgery, the skilled artisan will recognize that fistulas and/or ruptures caused by acute trauma, chronic conditions, etc. also can be treated with the methods and systems described herein. Furthermore, the terms "fistula," "stump leak fistula," "stump leak" and "leak" may be used interchangeably herein and refer generally to an opening in body tissue of an internal cavity and/or an organ (e.g., an opening in an airway, aortic defects, arterial defects, and ruptures/punctures in the walls of airways and/or blood vessels), which creates fluid communication between a cavity or organ and another cavity or organ within a patient or the external environment. The various embodiments described herein are not limited to airways and bronchi, and can be used to treat other body tissues and organs, including without limitation the esophagus, cardiac and pericardial tissue, blood vessels, intestines, bile ducts, sinuses, the cerebrospinal ventricular system, urinary bladders, and so forth.

Preferably, the embodiments disclosed herein are delivered using a delivery device. The embodiments disclosed herein, for example, may be packaged within the delivery device in a compressed state. The delivery device preferably has a working channel or other cavity configured to accommodate and facilitate the deployment of the embodiments described herein. In some embodiments, a delivery catheter or other secondary delivery device may be used to assist in the deployment of a treatment device. A delivery catheter, for example, may be inserted in the working channel of the delivery device. In such a situation, the delivery catheter preferably comprises a cavity or other means to accommodate and facilitate the deployment of a treatment device loaded therein. In some embodiments, the delivery catheter may have a treatment device attached at its distal tip.

Further, the delivery device preferably is provided with a visualization channel permitting navigation of the delivery device to a deployment site (e.g., into a patient's airway). Suitable delivery devices could include, for example, an endoscope with a working channel configured to access a patient's lungs via the patient's throat or other airway. The endoscope could be a commercially-available bronchoscope, such as the BR-P180 made by Olympus. Of course, endoscopes other than bronchoscopes may be used for procedures in other areas, and such endoscopes preferably will be provided with a working channel or other cavity for a treatment device.

Figure 1E:
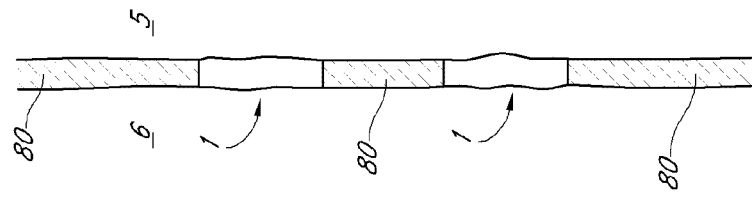
FIG. 1E is an elevated cross-section view of a series of fistulas in the side wall of a body lumen or cavity.
Figure 1D:
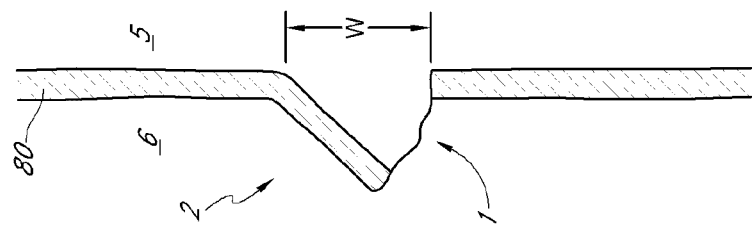
FIG. 1D is an elevated cross-section view of flap fistula in the wall of a body lumen or cavity.
Figure 1C:
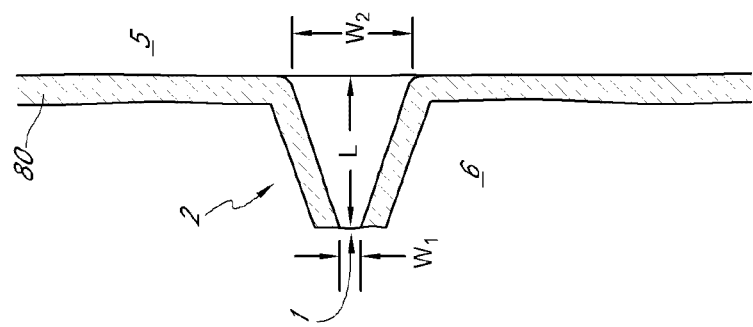
FIG. 1C is an elevated cross-section view of a tapered stump fistula in the side wall of a body lumen or cavity.

As explained above, stump leak fistulas refer generally to fistulas and/or ruptures in the lining of an airway or other organ/cavity within the body. Such fistulas/ruptures can create fluid communication between two or more organs or internal cavities within the body. FIGS. 1A-1E schematically illustrate different types of stump leak fistulas. FIG. 1A depicts a stump leak where the leak 1 has a stump that is flush with the surrounding tissue 80. Such a leak 1 could occur, for example, in the wall of an airway or in the barrier between the esophagus and trachea. The leak 1, as illustrated in FIG. 1A, could also occur in the sidewall of an airway within the lung. In some instances, the borders of a fistula 1 in a tissue wall 80 could take on many different shapes including, but not limited to, a linear slit, an irregular shape, a pin hole or other shapes.

Figure 1B:
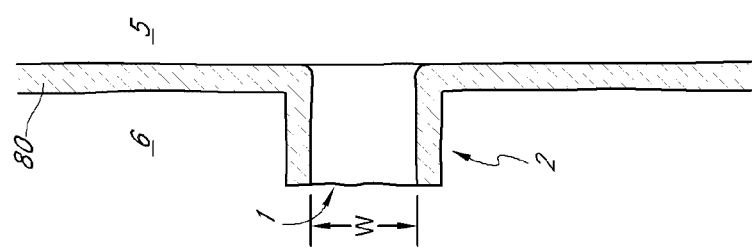
FIG. 1B is an elevated cross-section view of an extended stump fistula in the side wall of a body lumen or cavity.
Figure 1A:
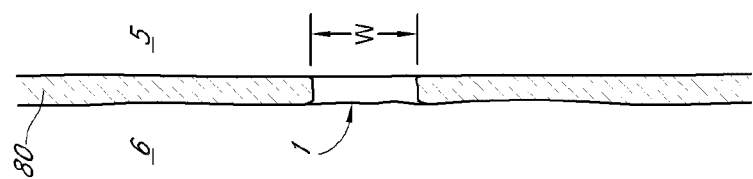
FIG. 1A is an elevated cross-section view of a fistula in the side wall of a body lumen or cavity.

FIG. 1B illustrates an extended stump leak 1 where the stump 2 has a width W and length L. While illustrated as a substantially cylindrical member, the stump 2 can be asymmetrical in configuration. The extended leak could occur, for example, at the end of an elongated airway or in the sidewall of an airway. Finally, FIG. 1C shows an extended tapered stump 2 where the stump 2 has a first and second width, $W_1$, $W_2$ and a length L. Like the extended stump leak 1 illustrated in FIG. 1B, a tapered stump could occur at the end of an elongated airway or in the sidewall of an airway.

FIG. 1D illustrates an asymmetric tissue, or "flap" fistula 1. Such a fistula could be caused by, for example, a puncture in the wall of an airway or blood vessel. In some circumstances, multiple fistulas 1 can occur in one area of a blood vessel or airway. This can be caused, for example, by a splitting in the seam of a suture. FIG. 1E illustrates an example of how such a fistula 1 may be presented.

The geometry of a stump 2 (if present) can help determine the device or treatment most appropriate for treating the stump leak 1. It will be understood that the fistulas illustrated in FIGS. 1A-E are schematic and for illustrative purposes, and that such a fistula encountered in, for example, a resected lung typically will not show such regular contours and shapes. Additionally, in practice such fistulas may present as hybrids of these types, or as different types not described here. Nonetheless, the embodiments disclosed herein are not intended to be limited to the treatment of only one type of fistula, and may, as appropriate, be used for the treatment of many diverse fistula types.

For example, stumps with elongated and/or tapered portions, as illustrated in FIGS. 2A-2C, can be treated with a plug 10. The plug 10 preferably comprises an expandable, substantially cylindrical or tapered body portion 13 with a port 14 on its proximal end. The port 14 can be configured to be fluidically connected to an inflation member 17. The inflation member 17 preferably is connected to the port 14 in a removable fashion, for example using a breakaway or twist-off connection. The plug 10 may be provided with a fixation aid, such as an adhesive configured to secure the plug to the surrounding tissue 80 in the wall of the airway 5. In an embodiment, the fixation aid on the plug 10 can comprise one or more anchors 12 that serve to fix or secure the plug 10 by extending into the tissue 80 surrounding the airway 5 so as to substantially inhibit movement of the plug 10. In some embodiments, the plug 10 could be constructed of a biocompatible material. Such materials could include, for example, water-based urethanes. In some embodiments, the plug 10 could be constructed of a biodegradable, dissolvable, or bioabsorbable material. In some embodiments, the plug 10 could be coated with a biocompatible material such as porous Teflon or a scaffold seeded with body tissue cells (e.g., stem cells, fibroblasts, chondrocytes) and/or appropriate growth factors, nutrients, antimicrobial compounds, anti-inflammatory compounds, and other such substances.

A method of implanting the plug 10 could include loading the plug 10 into the distal end of a delivery catheter 109 within the working channel 108 of a delivery device 100. The delivery device 100 then could be introduced to the site of the fistula 1, using a camera 102 or other suitable guidance instrumentation. The delivery catheter 109 containing the plug 10 could be positioned just inside the airway 5 from the fistula 1. The delivery catheter 109 may comprise the inflation member 17 at a distal end, which can connect to the proximal end of the plug 10. Once positioned, the plug 10 can be inflated with a liquid, gas, solidifying liquids (or any combination thereof) via the inflation member 17. In some embodiments, the plug 10 can be inflated or filled with hydro gels, cyanoacrylates, tissue-based or fibrinogen glues, or other substances suitable for inflating the plug 10. As it is inflated, the plug 10 can expand to substantially fill the airway space near the fistula 1. Once filled, the plug 10 can prevent all or substantially all air or other fluids from passing between the airway 5 and surrounding cavity 6. After inflation of the plug 10, the inflation member 17 can be disconnected from the plug 10 via, for example, a twisting or snapping motion, allowing the delivery catheter 109 and delivery device 100 to be withdrawn from the site of the fistula 1. In some embodiments, the plug 10 may be constructed from a resilient or self-expanding material (e.g., foam), either in combination with or as an alternative to the inflation member 17.

Another way of treating elongated or tapered stumps is with a plug apparatus 20, as illustrated in FIG. 3A-3B. A plug apparatus 20 can comprise a central, expandable solid plug 23. The solid plug 23 is configured to fixedly attach to two expandable conical portions 21. In some embodiments, the solid plug 23 can be constructed from flexible materials, including polymers such as polycarbonate, urethane, nylon, and combinations thereof. In some embodiments, the solid plug 23 can be constructed of porous polytetrafluoroethylene. In some embodiments, the solid plug 23 and/or conical portions 21 can be constructed from bioabsorbable or biodegradable materials which could dissolve over time. The conical portions 21 are configured to expand radially into the interior of an airway 5 or other internal lumen. In some embodiments, the conical portions 21 can be constructed of a flexible material, such as a polymer. In some embodiments, the polymer is nylon, urethane, polycarbonate, polyethylene or other suitable materials, copolymers, mixtures or combinations thereof.

The plug apparatus 20 can be delivered to the site of a fistula 1 in a compressed configuration via a delivery catheter 109 introduced via the working channel 108 of a delivery device 100. Upon withdrawal of the delivery device 100, the central solid plug 23 and conical portions 21 expand radially to fill the radius of the stump 2. Thus, the two conical portions 21 act to provide both longitudinal and axial stability to the central solid plug 23. Once implanted, air may be substantially prevented from passing around and/or through the central plug 23. In this manner, the plug apparatus 20 can substantially seal the airway 5 from the surrounding cavity 6. In some embodiments, the plug apparatus 20, as illustrated in FIG. 3C, can be used to treat wall fistulas 1 similar to the fistula illustrated in FIG. 1A. In such an embodiment, the central solid plug 23 could fill the fistula 1 and be held in place by the two conical portions 21. Additionally or alternatively, the central plug 23 could comprise radial anchors configured to engage with the surrounding tissue 80 of the wall fistula 1.

Figure 4:
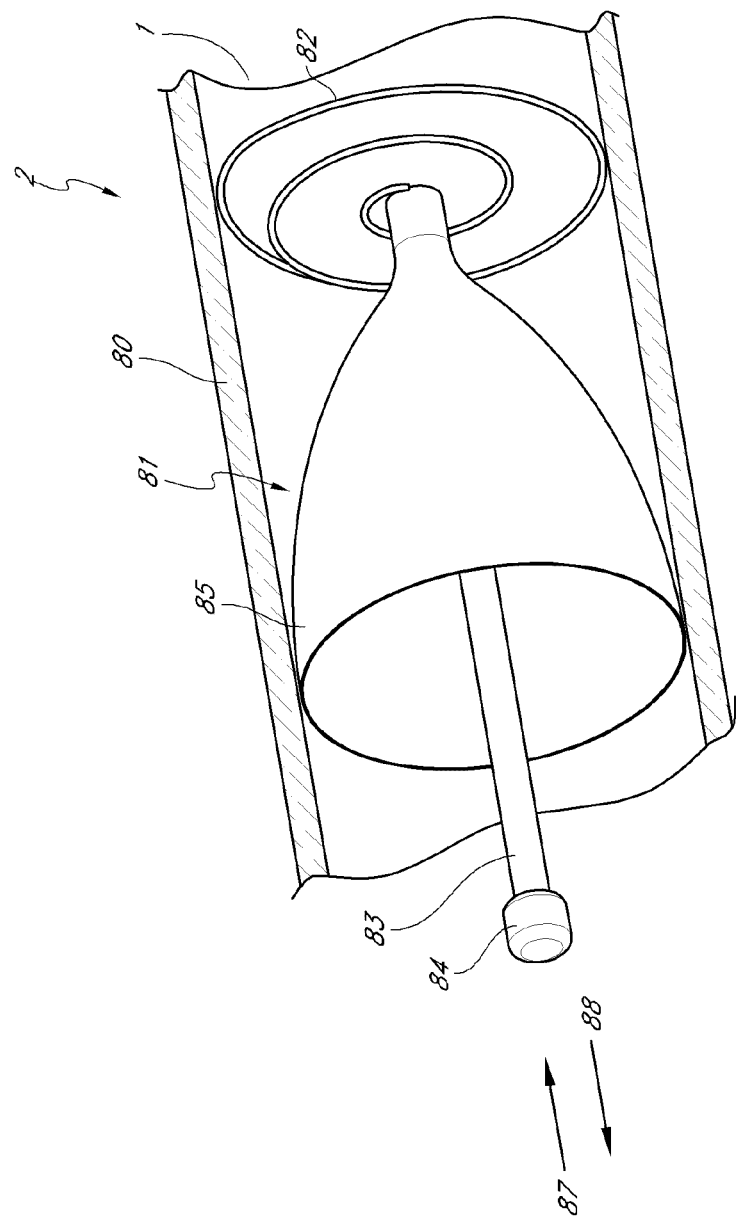
FIG. 4 is a perspective view of an embodiment of a cone valve with a spiral anchor within a stump.

As illustrated in FIG. 4, an embodiment of a conical valve 81 can comprise a proximal knob 84 connected to a central rod 83. The central rod 83 can be connected to a cone portion 85. In some embodiments, the distal end of the central rod 83 is connected to a spiral anchor 82. Upon introduction to the site of a fistula leak 1, the conical portion 85 and spiral anchor 82 of the conical valve can expand to fill the interior space 5 of an elongated stump 2. In some embodiments, fluid flow in a first proximal to distal direction 87 will impinge upon the inner surface of the conical portion 85 of the conical valve 81. This impingement could cause the conical portion 85 to exert radial pressure on the surrounding tissue 80 and thus effectively block the airway 5 and inhibit fluid flow past the conical valve 81 when fluid flows in the first direction 87. In some embodiments, fluid flow in a second distal to proximal direction 88 can impinge upon the outer surface of the conical portion 85 of the conical valve 81. This impingement can cause the conical portion 85 of the conical valve 81 to partially collapse. Such a partial collapse could allow fluid to flow past the conical valve 81 in the second direction 88. In some embodiments, the conical valve 81 can thus be used as a one-way valve to treat the fistula 1. In some embodiments, portions of the conical valve 81 could be constructed of a biocompatible material. For example, the spiral anchor 82 could be constructed of a biocompatible material. Biocompatible materials could include, for example, porous Teflon/PTFE. Such a material could promote the ingrowth of tissue into the pores. Use of biocompatible materials could allow for long term/permanent implantation of the conical valve 81.

Other anchor configurations, such as a plurality of anchors of anchors with piercing ends that extend radially outward from the central rod 83 and/or from the cone portion 85, can also be used. Such radially-extending anchors could be configured to pierce the tissue 80 surrounding the stump 2 to hold the conical valve 81 in place within the airway and/or stump 2. The depth to which the anchor ends pierce the tissue 80 can be limited by pads or other limiting structures on the anchors.

Figure 5A:
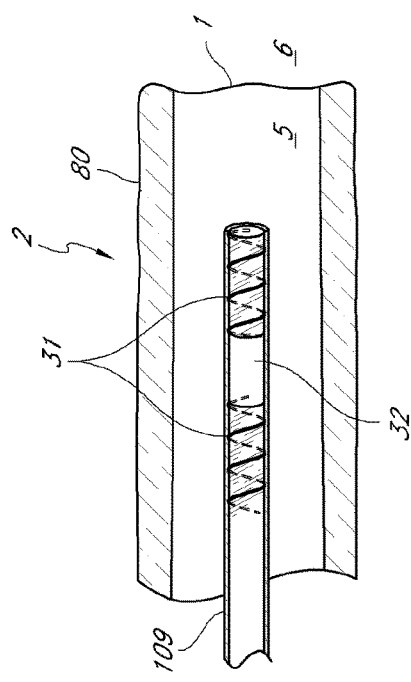
FIG. 5A is a perspective view of an embodiment of a double spiral valve within a delivery catheter.
Figure 5B:
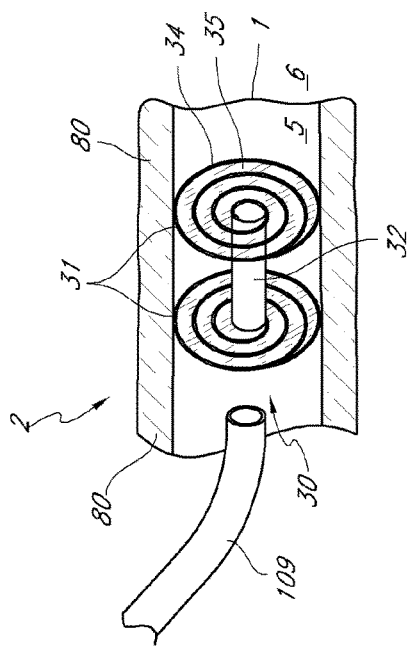
FIG. 5B is a perspective view of the double spiral valve of FIG. 5A deployed in a stump.

FIGS. 5A-5B illustrate another embodiment of a device which can be used to treat an elongated or tapered stump leak. A dual-spiral apparatus 30 can comprise a central hub 32. Preferably, the central hub 32 is attached to two spiral portions 31, one on each end of the central hub 32. Each of the spiral portions 31 can comprise a framing portion 34 and a membrane 35 attached to the framing portion 34. The framing portions 34 can connect to the central hub 32. In some embodiments, the framing portions 34 comprise a shape memory material or otherwise springy/resilient material that can facilitate expansion of the framing portion 34 into an airway 5. The membrane 35 can be stretched over the framing portion 34 to provide coverage of the airway 5. Thus, the dual-spiral apparatus 30 can, according to some embodiments, substantially prevent fluids from bypassing the dual-spiral apparatus 30. The framing portions 34 can expand to varying sizes, allowing use of the dual-spiral apparatus 30 in multi-radius body lumens. In some embodiments, the membrane 35 could be constructed of a flexible material, such as a polymer. In some embodiments, the polymer is nylon, urethane, polycarbonate, polyethylene or some other suitable materials, copolymers, mixtures or combinations thereof. In some embodiments, the framing portions 34 can be constructed from a resilient material, such as electropolished nitinol, electropolished stainless steel, or some other material suitable for implantation in the body and structural support of the apparatus 30.

In a preferred embodiment, the dual-spiral apparatus 30 may be implanted by delivering the apparatus to the site of a fistula 1 in a compressed state via a delivery catheter 109 in the working channel 108 of a delivery device 100. FIG. 5A illustrates an embodiment of the dual-spiral apparatus 30 compressed within a delivery catheter 109. When compressed, the spiral portions 31 form tight spirals within the delivery catheter 109. The dual-spiral apparatus 30 can be deployed into an airway 5 by pushing the apparatus 30 out of the distal end of a delivery catheter 109 or some other delivery device. Upon deployment of the dual-spiral apparatus 30 into an airway 5 or other body lumen, the spiral portions 31 expand radially, thus allowing the membrane 35 to substantially block fluid flow through the body lumen.

Figure 6C:
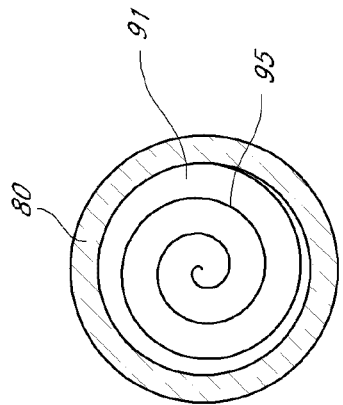
FIG. 6C is a front view of the spiral valve of FIG. 6A deployed in a stump.
Figure 6B:
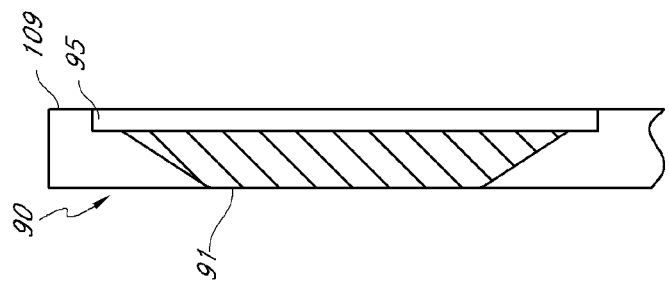
FIG. 6B is a side view of the spiral valve of FIG. 6A compressed within a delivery catheter.
Figure 6A:
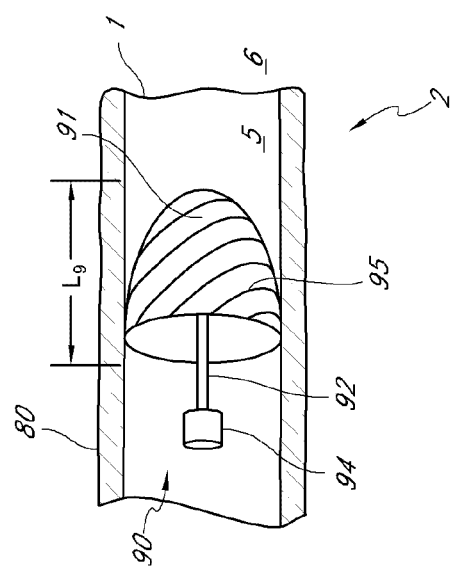
FIG. 6A is a perspective view of an embodiment of a spiral valve deployed in a stump.

Another embodiment of a spiral apparatus suitable for treating elongated stump leaks 1 is illustrated in FIGS. 6A-6C. Preferably, a spiral plug 90 comprises a central rod 92, a proximal knob 94, a frame portion 95, and a membrane 91. The frame portion 95 is configured to attach to the distal end of the central rod 92. The frame portion 95 also is configured to expand radially and/or proximally from the central rod 92 to form a conical, hemispherical or disc-like shape. The frame portion 95, in some embodiments, can be constructed of a springy resilient material such as, for example, polymers or metals, preferably shape-memory alloys (e.g., Nitinol). In some embodiments, the membrane 91 could be constructed from a flexible material, such as a polymer. In some embodiments, the polymer is nylon, urethane, polycarbonate, polyethylene or other suitable materials, copolymers, mixtures or combinations thereof. The proximal knob 94 is configured to attach to the proximal end of the central rod 94.

Preferably, the spiral plug 90 is implanted by loading the plug into the distal end of a delivery catheter 109 and delivering the plug 90 to the site of a fistula 1 via the delivery catheter 109 in the working channel 108 of a delivery device 100. FIG. 6B illustrates an embodiment of the spiral plug 90 as configured within a delivery catheter 109. Upon deployment from the delivery catheter 109, the frame portion 95 of the spiral plug 90 will expand in the radial direction to substantially fill an inside area of a stump 2. The expanded membrane 91 can fill or substantially fill the airway 5, inhibiting fluids from bypassing the spiral plug 90. In this manner, the interior of the airway 5 can be substantially sealed from the cavity 6 surrounding the exterior of the stump 2. The length $L_9$ of the spiral plug 90 can vary such that the membrane spiral plug 90 could comprise a thin disc configuration or, as illustrated in FIG. 6A, a conical configuration. One potential advantage of a conical configuration could be increased stability of alignment of the spiral plug 90 within an airway 5 or other body lumen. FIG. 6C shows an end-view of an embodiment of the spiral plug 90 in an expanded configuration. In some embodiments, the spiral plug 90 can include one or more anchoring structures (e.g., spiral anchors, tissue-piercing anchors) configured to inhibit the spiral plug 90 from translating proximally and/or distally within the airway 5 upon implantation of the spiral plug 90 into the airway 5.

An additional embodiment of a spiral apparatus suitable for treating elongated stump leaks 1 is shown in FIGS. 7A-7E. A spiral valve 110 can comprise a central hub 114 connected to one or more frame members 115. In some embodiments, the spiral valve 110 includes a valve flap 113 attached to the one or more frame members 115. In some expanded configurations, the valve flap 113 and one or more frame member 115 of the spiral valve 110 can be distributed in a spiraling pattern after deployment, as shown in FIG. 7A. FIG. 7E is a cross-sectional view of an embodiment of the valve flaps 113 along the cut plane E-E of FIG. 7A. In some embodiments, the valve flap 113 is configured to overlap itself as it unfurls (as shown in FIGS. 7A and 7E). According to some configurations, when fluid flows in a proximal to distal direction 117 toward the spiral valve 110, each portion of the valve flap 113 moves toward a radially-adjacent portion of the valve flap 113. Such movement can create a seal between the radially-adjacent portions of the valve flap 113. As a result of this movement, the valve flap 113 can substantially inhibit fluid flow through the spiral valve 110 in a proximal to distal direction 117.

In some embodiments, when fluid flows in a distal to proximal direction 118, each portion of the valve flap 113 can be deflected away from a radially-adjacent valve flap 113. Thus, according to some configurations, valve flap 113 can allow fluid flow through a spiral valve 110 in a distal to proximal direction 118. Some embodiments of the spiral valve 110 can thus allow for one-way inhibition of fluid flow through a fistula in an airway 5 or other body lumen. Such an embodiment of a spiral valve 110 could, for example, permit air from the cavity 6 surrounding the stump 2 to pass through the valve 110 during exhalation from the lung. In some such embodiments, air from the airway 5 could be substantially prevented from entering the cavity 6 during inhalation. This one-way inhibition of fluid flow could help reduce the likelihood of the development of pneumothoraces within a patient's pleural cavity. In some embodiments, the valve flap 113 can be constructed from a flexible material, such as a polymer. In some embodiments, the polymer is nylon, urethane, polycarbonate, polyethylene or other suitable materials, copolymers, mixtures or combinations thereof.

A method of implanting the spiral valve 110 can include delivering the valve in a compressed state via a delivery catheter 109, as shown in FIG. 7D. When in a compressed state within a delivery catheter 109, the valve flap 113 of the spiral valve 110 can remain in an unfurled configuration. FIG. 7B illustrates an end-view of the spiral valve 110 within a delivery catheter 109. As shown, one side of the valve flap 113 can be attached to a frame member 115. FIG. 7D shows a side view of the compressed spiral valve 110. Upon withdrawal of the delivery catheter from the spiral valve 110, the one or more frame members 115 can expand radially toward the inner surface of the stump 2, as illustrated in FIGS. 7A and 7C.

FIGS. 8A and 8B illustrate an embodiment of a spiral valve 120 which is similar to the spiral valve 110 described above. The spiral valve 120 can comprise a central hub 124 which can be connected to one or more frame portions 125. In some embodiments, the spiral valve 120 includes a valve flap 123 attached on one side to the one or more frame portions 125. The spiral valve 120 can include an anchor barb 121 attached to the end of one or more of the frame portions 125.

FIG. 8B shows an embodiment of the spiral valve 120 in a compressed state within a delivery catheter 109. When the spiral valve 120 is delivered to the site of a fistula 1 in a stump 2, the anchor barb 121 can secure the spiral valve 120 to the surrounding tissue 80 of the airway as the spiral valve 120 unfurls. In some embodiments, the anchor barb 121 could be used in combination with a spiral valve 110, a spiral plug 90, a dual-spiral apparatus 30 or any similar device. According to some configurations, the anchor barb 121 can at least partially prevent a device from spinning within an airway when deployed, thus providing for greater control in the delivery of a spiral valve or spiral plug. Further, anchor barbs 121 as described above could be utilized with other embodiments of devices described herein.

Figure 9A:
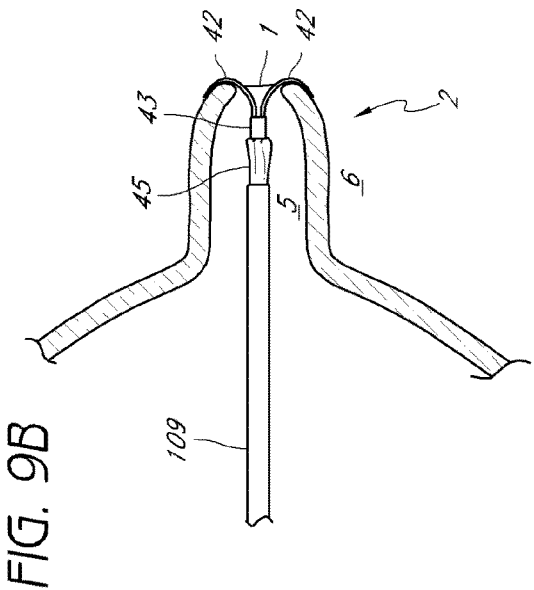
FIG. 9A is a side view of an embodiment of a cone valve within a delivery catheter at the site of a stump, the anchors of the cone valve having been partially pushed out from the delivery catheter.
Figure 9B:
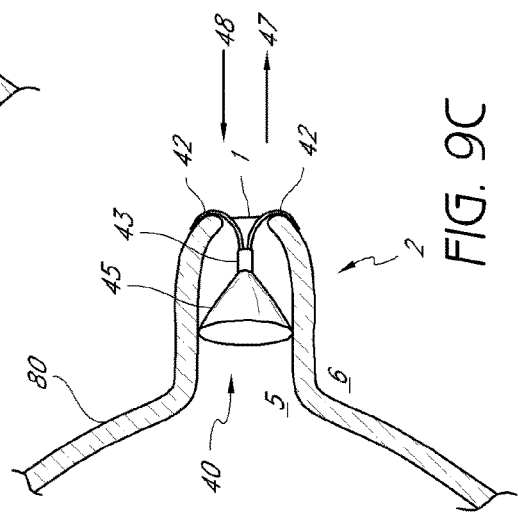
FIG. 9B is a side view of the cone valve of FIG. 9A, further removed from the delivery catheter.
Figure 9C:
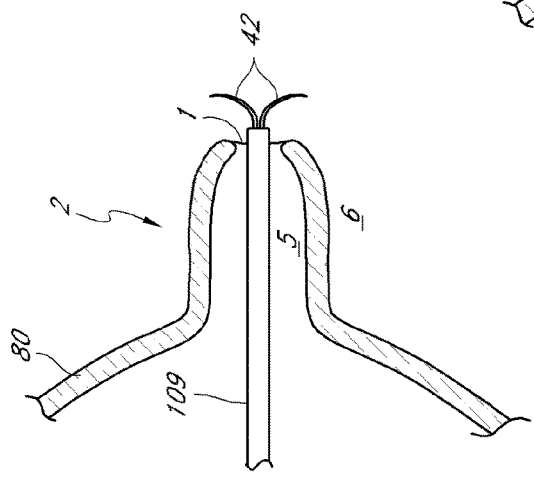
FIG. 9C is a side view of the cone valve of FIG. 9A, deployed in a stump.

FIGS. 9A-9C illustrate an embodiment of a conical valve 40 which can be used to treat, for example, elongated and/or tapered stump leak fistulas 1, similar to fistulas illustrated in FIG. 1C. The conical valve 40 preferably comprises a central hub 43. The proximal end of the central hub 43 can be configured to attach to a conical portion 45 surrounding a central rod 46. The proximal end of the central rod 46 can be configured to attach to a proximal knob. The distal end of the central hub 43 also may comprise a plurality of anchors 42. In some embodiments, the conical portion 45 of the conical valve 40 can be configured to expand radially to substantially fill an airway 5 or other body lumen. Additionally, the plurality of anchors 42 can be configured to expand radially and wrap around the end of a stump leak 2, as illustrated in FIGS. 9B and 9C. In some embodiments, additional anchors 42 can be used to distribute the anchoring force over a larger area in order to help reduce the risk of tissue damage in the vicinity of the anchors. In some embodiments, the conical portion 45 could be constructed from a flexible material, such as a polymer. In some embodiments, the polymer is nylon, urethane, polycarbonate, polyethylene or other suitable materials, copolymers, mixtures or combinations thereof. In some embodiments, the central hub 43 can be constructed of a biocompatible material, such as porous Teflon. In some embodiments, the central hub 43 and/or conical portion 45 can be constructed from biodegradable materials, which could dissolve over time.

A method of implanting a conical valve 40 can include delivering the valve in a compressed state via a delivery catheter 109 to the site of a fistula 1. As illustrated in FIG. 9A, the conical valve 40 can be pushed out from the distal end of the delivery catheter 109, allowing the anchors 42 to expand radially and effectively wrap around the distal end of a stump leak 2. In some embodiments, the delivery catheter 109 is then withdrawn from the conical valve 40, as illustrated in FIGS. 9B-9C. As the delivery catheter 109 is withdrawn from the conical valve 40, the conical portion 45 can expand radially, thereby substantially filling the airway 5 or other body lumen, as illustrated in FIG. 9C. In some embodiments, the conical valve 40 can be configured to function as a one-way valve, as described above with reference to the conical valve 81.

Another embodiment of a cone valve 60 capable of treating elongated and/or tapered stumps is illustrated in FIGS. 10A and 10B. The cone valve 60 preferably can comprise a proximal knob 64 attached to a central rod 66. The central rod 66 can be fixedly attached to a central hub 63. In some embodiments, the cone valve 60 includes a conical portion 65 attached to the central hub 63 and surrounding some portion of the central rod 66. The cone valve can further include one or more anchors 62 attached to the central hub 63. Additionally, in some embodiments, the cone valve 60 further may comprise atraumatic portions 69 attached to the distal ends of the anchors 62. The atraumatic portions 69 can comprise loops, spherical portions, ellipses, or other geometries that apportion pressure to tissue 80 over an area larger than the cross-section area of the anchors 62. For example, FIGS. 10A and 10B illustrate an embodiment where the atraumatic portions 69 are loops of material. Atraumatic portions 69 can be included on the anchors of the embodiments of the valves and plugs described above or below.

Figure 11:
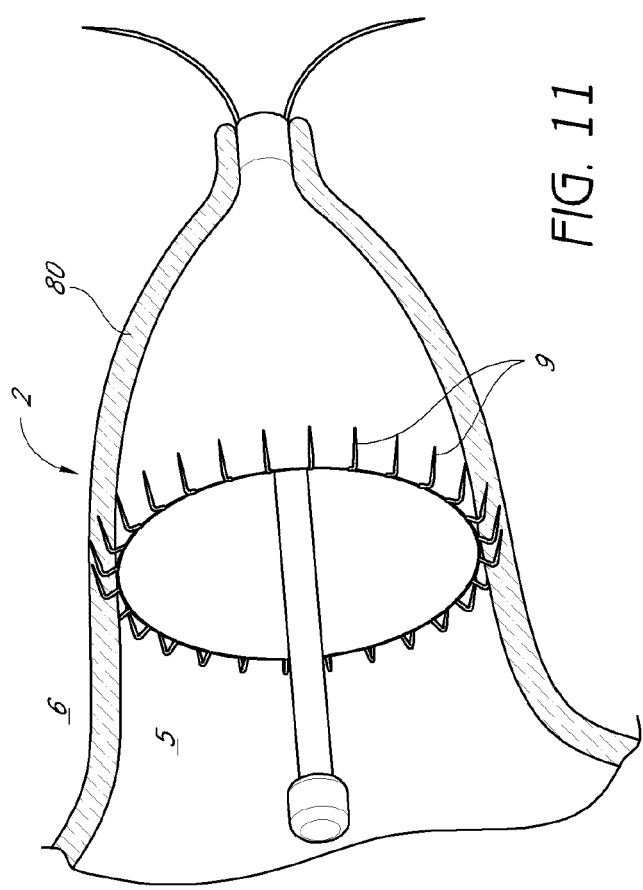
FIG. 11 is a perspective view of an embodiment of a cone valve with a plurality of anchors around the lip of the cone portion, the cone valve deployed in a stump.

In some embodiments, the atraumatic portions 69 can be constructed of the same material as the anchors 62. Additionally or alternatively, the atraumatic portions 69 could form a unitary part with the anchors 62. The atraumatic portions 69 can help to reduce trauma to the tissue 80 onto which the anchors 62 attach, and are preferably rounded or tipped with a soft material. Additionally or alternatively, any of the embodiments of a cone valve or conical valve described above or below could comprise one or more anchors 9 around the periphery of the proximal end of a conical portion of a cone or conical valve, as illustrated in FIG. 11.

FIGS. 12A-12C illustrate an embodiment of a cone valve 130 which preferably can be used to treat a tapered stump leak 1. The cone valve 130 can comprise a central hub 134. In some embodiments, the proximal end of the central hub 134 attaches to one or more of anchors 132. The distal end of the central hub 134 can be configured to attach to a central rod 136. The distal end of the central rod 136 could be configured to attach to a conical portion 135.

A method of implanting the cone valve 130 can include deploying the valve 130 to the site of a tapered stump fistula 1 in a compressed configuration via a delivery catheter 109 inserted in the working channel 108 of a delivery device 100. Accordingly, the conical portion 135 of the cone valve 130 can be introduced into the cavity 6 surrounding a stump 2 via the distal end of the delivery catheter 109. The delivery catheter 109 is withdrawn from the conical portion 135, after which the conical portion 135 expands radially. The delivery catheter 109 or another suitable implement then may be used to pull the cone valve 130 back toward the airway 5, thus permitting the conical portion 135 of the cone valve 130 to surround the open end of the stump 2. The delivery catheter 109 of the delivery device 100 then is completely withdrawn, freeing the central hub 134 and the anchors 132. The anchors 132 may be configured to expand radially toward the tissue 80 surrounding the fistula 1, and preferably are configured to point distally radially-outward from the central hub 134, thereby creating acute angles between the anchors 132 and the central rod 136 of the cone valve 130. The anchors 132 can be configured to engage with the surrounding tissue 80. In some configurations, the anchors 132 reduce the likelihood of movement of the cone valve 130 in the direction of the surrounding cavity 6, which can help the conical portion 135 of the cone valve 130 create a two-way seal around the fistula 1.

FIGS. 13A-13I illustrate an embodiment of a double cone valve 190 and push-pull mechanism 105 which can be used to treat a tapered stump leak 1. The double cone valve 190 preferably comprises a central hub 193. The proximal end of the central hub 193 can be configured to attach to a central rod 196 and a first conical portion 195A. The first conical portion 195A can be configured to expand in a radial direction and to attach to the central hub 193. The double cone valve 190 can further comprise a first proximal knob 194A configured to slidably attach to the central rod 196 such that the proximal knob 194A can move in a distal and/or proximal longitudinal direction with respect to the central rod 196, but preferably not in a torsional or radial direction (e.g., spinning or disengaging from the central rod 196) with respect to the central rod 196. The proximal end of the first proximal knob can be configured to attach to a second conical portion 195B. The second conical portion 195B can be configured to expand radially and also to attach to the first proximal knob 194A. The proximal end of the central rod 196 could be configured to attach to a second proximal knob 194B.

In some embodiments, the push-pull mechanism 105 can comprise an engagement portion 103 which can grasp and/or pull the proximal knob 194B of the conical valve 190. In some embodiments, the outer sheath 109A of a delivery catheter 109 can be configured to move independently from the push-pull mechanism 105. As illustrated in FIG. 13G, some configurations of a push-pull mechanism 105 may comprise an engagement portion 103 with a hook mechanism 103A. In some embodiments, the hook mechanism 103A can be configured to releasably engage with the second proximal knob 194B and the central rod 196 of the double cone valve 190. Such engagement between the hook mechanism 103A and the second proximal knob 194B can enable a user to move the second proximal knob 194B with respect to the outer sheath 109A of a delivery catheter 109. In some embodiments, an engagement member 103 can comprise a plurality of finger members 103B, as illustrated in FIGS. 13H-13I. The plurality of finger members 103B can be configured to releasably engage with the second proximal knob 194B and the central rod 196. Such engagement between the plurality of finger members 103B and the second proximal knob 194B can enable a user to pull or move the knob 194B with respect to the outer sheath 109A of the delivery catheter 109. In some embodiments, the plurality of finger members 103B can be released from the second proximal knob 194B by withdrawing the finger members 103B from the interior of the delivery catheter 109, as illustrated in FIGS. 13H and 13I.

A method of implanting the double cone valve 190 can include delivering the valve 190 in a compressed configuration to the site of a stump leak 1 via a delivery catheter 109 within a working channel 108 of a delivery device 100, as illustrated in FIG. 13A. The distal end of the delivery catheter 109 can be positioned within the cavity 6 surrounding the fistula 1. The delivery catheter can then be withdrawn from the first conical portion 195A, as illustrated in FIG. 13B. Upon exiting the delivery catheter 109, the first conical portion 195A can expand radially into the surrounding cavity 6.

After the first conical portion 195A expands, the delivery catheter 109 can be withdrawn from the second conical portion 195B, allowing the second conical portion 195B to expand radially into the interior airway 5 of the stump leak 2, as illustrated in FIG. 13C. The push-pull mechanism 105 in the delivery catheter 109 can be used to pull the first conical portion 195A onto the outer surface of the stump leak 2 while the first conical portion 195B is pushed into the inner surface of the stump leak 2, as illustrated in FIG. 13D. In some arrangements, the outer sheath 109A of the delivery catheter 109 can push the inner surface of the second conical portion 195B of the double cone valve 190.

As illustrated in FIG. 13F, the first proximal knob 194A of the double cone valve 190 may comprise a ratchet mechanism 104. In some embodiments, the ratchet mechanism 104 has a hinge point 104A fixedly attached to the central rod 196 and that can bias the ratchet mechanism 104 away from the central rod 196. In some configurations, the ratchet mechanism 104 hinges about the point 104A and reduces the likelihood of movement of the first proximal knob 194A in a proximal direction along the central rod 196 once the ratchet mechanism 104 has been pulled outside the first proximal knob 194A. In some embodiments, the ratchet mechanism has a hinge point 104B fixedly attached to the first proximal knob 194A and thereby can bias the ratchet mechanism 104 toward the central rod 196. In some configurations, the central rod 196 can comprise grooves configured to engage the ratchet mechanism 104. In some embodiments, engagement between the ratchet mechanism 104 and grooves on the central rod 196 inhibit translation of the first proximal knob 194A in the proximal direction with respect to the central rod 196.

In some configurations, as illustrated in FIGS. 13C-13D, the push-pull mechanism 105 and engagement portion 103 can be used to pull the second proximal knob 194B away from the fistula 1, which can result in the movement of the first conical portion 195B of the double cone valve 190 from the exterior cavity 6 toward the fistula 1. At the same time, the outer sheath 109A of the delivery catheter 109 can be held in place on the interior surface of the second conical portion 195B, as illustrated in FIG. 13E. In such a configuration, the second conical portion 195B can be held in place in the inside of the stump leak 2 while the first conical portion 195A is pulled toward the stump leak fistula 1. In some embodiments, the ratchet mechanism 104 on the first proximal knob 194A can inhibit the second conical portion 195B from moving away from the first conical portion 195A.

FIGS. 14A-14C illustrate a device that can be used to treat tapered stump fistulas or extended stump fistulas. In some embodiments, a barbed anchor 160 comprises a central rod 166 attached to a helical barbed member 162. The barbed anchor 160 may be introduced to the site of a stump leak 2 such that the helical barbed member 162 can puncture the tissue 80 surrounding the fistula 1. The central rod 166 of the barbed anchor 160 can be moved (e.g., rotated) so that the tissue 80 surrounding the barbed valve 160 engages with the helical barbed member 162 and is drawn onto or over the central rod 166. According to some embodiments, the tissue 80 surrounding the stump 2 can be drawn tightly or cinched (e.g., by rotation of the central rod 166) to close proximity with central rod 166 of the barbed anchor member 160, thereby substantially sealing the fistula 1 and reducing the likelihood of the passage of fluid between the interior airway 5 and the surrounding cavity 6.

Figure 15B:
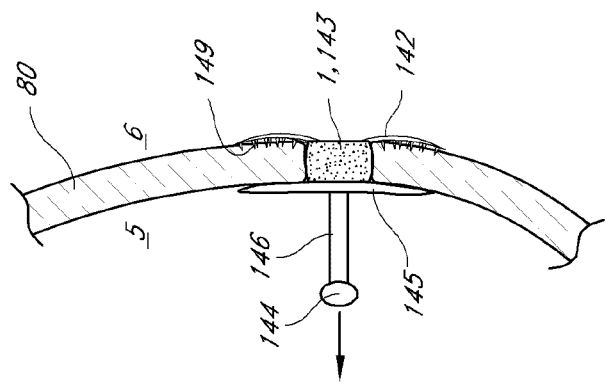
FIG. 15B is a side view of the cone valve of FIG. 15A fully deployed in a side wall fistula.
Figure 15A:
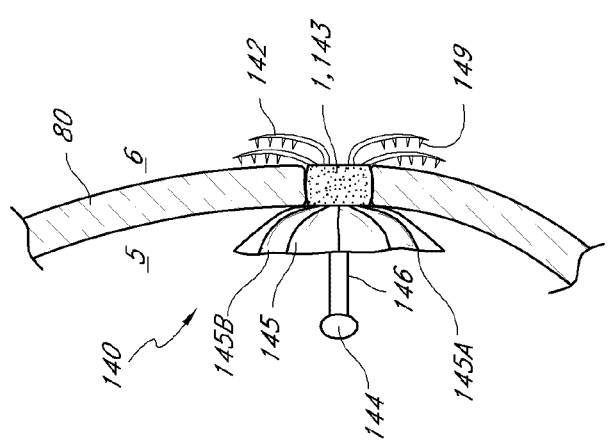
FIG. 15A is a side view of an embodiment of a cone valve partially deployed in a side wall fistula.

FIGS. 15A-15B illustrate an embodiment of a conical valve 140 that can be used to treat, for example, fistulas similar to those illustrated in FIG. 1A, or fistulas in the wall between the trachea and esophagus (i.e., tracheoesophageal fistulas). In some embodiments, the conical valve 140 comprises a central hub 143. The distal end of the central hub 143 is configured to attach to a plurality of anchors 142. The proximal end of the central hub 143 is configured to attach to a conical portion 145 and a central rod 146. In some embodiments, the anchors are configured to expand radially. In some embodiments, the plurality of anchors 142 hinge about a central point of the central hub 143. One or more of the plurality of anchors 142 comprises a plurality of barbs 149. The barbs 149 are configured to engage with the tissue 80. The conical portion 145 of the valve 140 can be configured to expand in the radial direction. In some embodiments, the conical portion 145 can comprise a plurality of frame portions 145A and a plurality of membrane portions 145B. In some embodiments, the plurality of frame portions 145A can be attached to the central rod 146 and hinge points within the central hub 143 and point radially-outward from the central rod 146. The proximal end of the central rod 146 can attach to a proximal knob 144.

A method of implanting the conical valve 140 can include deploying the valve to the site of a wall fistula 1 such that the central hub 143 of the conical valve is placed within the wall fistula 1. The proximal knob 144 can be pulled, as illustrated in FIG. 15B. The pulling of the proximal knob 144 can result in a "cinching" of the plurality of anchors 142 by pulling the outer radial portions of the anchors 142 in the proximal direction with respect to a central hinge point in the central hub 143. In some embodiments, pulling the proximal knob 144 in the proximal direction can cause cinching of the conical portion 145 by causing the frame portions 145A to hinge about hinge points within the central hub 143. This cinching can pull the anchors 142 and the conical portion 145 toward each other and toward the tissue 80 surrounding the fistula 1. The conical portion 145 and/or anchors 142 can include ratcheting mechanisms configured to inhibit the conical portion 145 and/or anchors 142 from returning to an "uncinched" configuration. In some embodiments, one or more barbs 149 on the plurality of anchors 142 can help secure the conical valve 140 to the site of the fistula 1, as shown in FIG. 15B.

Figure 16A:
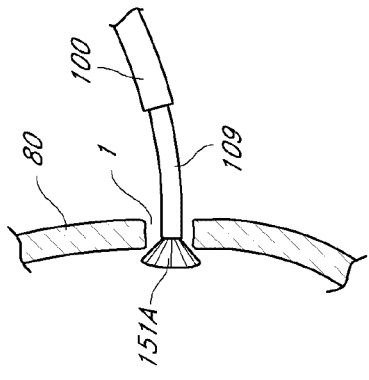
FIG. 16A is a side view of an embodiment of a double cone valve with a first cone partially removed from a delivery catheter at the site of a side wall fistula.
Figure 16B:
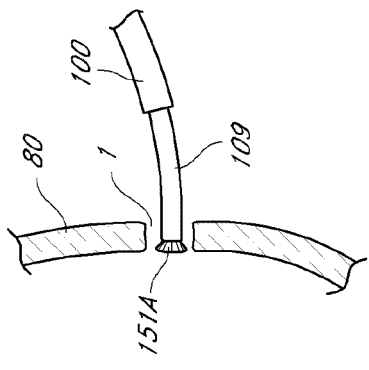
FIG. 16B is a side view of the double cone valve of FIG. 16A with the first cone further removed from the delivery catheter.
Figure 16C:
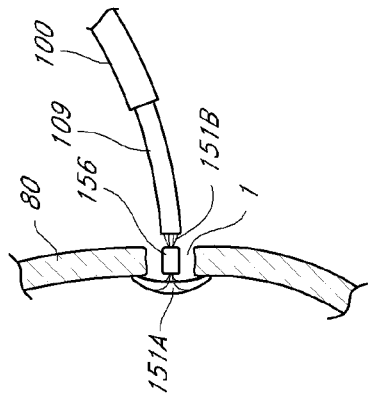
FIG. 16C is a side view of the double cone valve of FIG. 16A with the first cone and central hub removed from the delivery catheter.
Figure 16D:
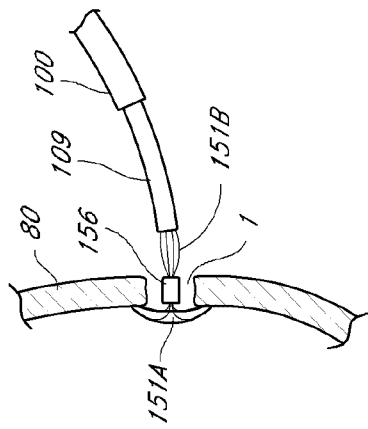
FIG. 16D is a side view of the double cone valve of FIG. 16A with the first cone, central hub and part of the second cone remove from the delivery catheter.
Figure 16E:
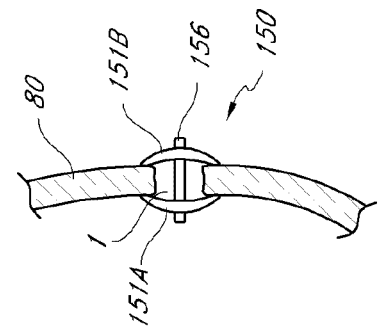
FIG. 16E is a side view of the double cone valve of FIG. 16A fully removed from the delivery catheter.

An embodiment of a two-sided conical valve 150 is illustrated in FIGS. 16A-16E. As illustrated in FIG. 16E, the two-sided conical valve 150 can comprise a central rod 156, wherein the distal and proximal ends of the central rod 156 are configured to attach to a first conical portion 151A and a second conical portion 151B, respectively. Conical portions 151A, 151B could comprise flexible membranes drawn over resilient and/or rigid frames. In some embodiments, the conical portions 151A, 151B could be similar or identical to the conical portion 145 of the conical valve 140, described above. The conical portions could be constructed from a flexible material, such as a polymer. In some embodiments, the polymer is nylon, urethane, polycarbonate, polyethylene or other suitable materials, copolymers, mixtures or combinations thereof. In some embodiments, the conical portions 151A, 151B are constructed of a semi-rigid material. The proximal end of the first conical portion 151A and the distal end of the second conical portion 151B can be configured to expand radially, thus comprising two cones that face each other. In some configurations, the two-sided conical valve 150 is configured to allow the first conical portion 151A and/or the second conical portion 151B to be adjustable in position with relation to each other and to the central rod 156.

As illustrated in FIGS. 16A-16B, a two-sided conical valve, according to some embodiments, may be delivered to the site of a fistula 1 in a compressed configuration via a delivery catheter 109 inserted in the working channel 108 of a delivery device 100. As shown in FIGS. 16B and 16C, the first conical portion 151A could be pushed from the delivery catheter 109 and expanded on one side of a fistula 1, while the second conical portion 151B remains in the delivery catheter 109. The second conical portion 151B then can be pushed from the delivery catheter 109 on a side of the fistula opposite the first conical portion 151A. Thus, according to some embodiments of a fully-deployed two-sided conical valve, the first conical portion 151A and the second conical portion 151B can substantially seal a fistula 1 from two sides. Additionally, according to some embodiments, the first conical portion 151A and/or the second conical portion 151B can be configured to have a low profile with respect to the tissue 80 surrounding the fistula 1. In some embodiments, the two-sided conical valve 150 can be constructed of biocompatible materials and could be a permanent implant. In some embodiments, portions of the two-sided conical valve 150 (e.g., the central rod 156) could be constructed of a biocompatible material such as, for example, porous Teflon/PTFE. Such a material could promote the ingrowth of tissue into the pores. Use of biocompatible materials could allow for long term/permanent implantation of the two-sided conical valve 150.

Figure 17:
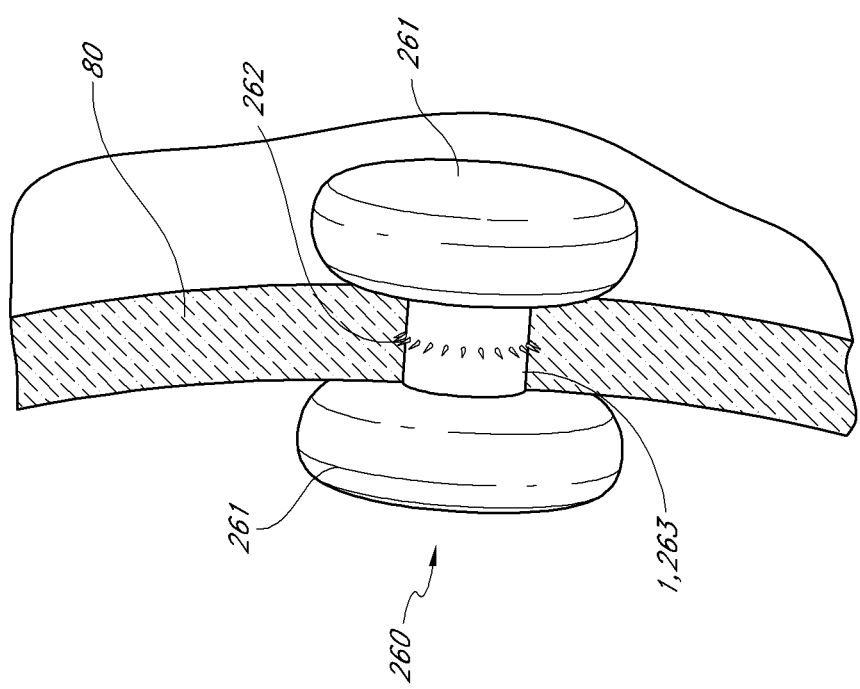
FIG. 17 is a perspective view of an embodiment of a two-sided plug deployed in a side wall fistula.

In some cases, a two-sided plug 260 could be used to seal a wall fistula 1, as illustrated in FIG. 17. In some embodiments, a two-sided plug 260 comprises a central hub 263. The distal and proximal ends of the central hub 263 can be configured to attach to two plug portions 261 In some embodiments, the material used to construct the central hub 263 could be thicker and/or stiffer than the material used to construct the two plug portions 261. In such an embodiment, upon inflation of the two-sided plug 260, the two plug portions 261 could expand further and/or more rapidly than the central hub 263. Further expansion of the two plug portions 261 could allow the two plug portions 261 to expand beyond the boundaries of the fistula 1 while the central hub 263 remains within the fistula 1. In this way, the two plug portions 261 could seal the fistula 1 from two sides. In some embodiments, the central hub 263 can exert a radially-outward force upon the walls of the fistula 1 to enhance and/or create a seal of the fistula 1.

In some embodiments, the two-sided plug 260 could be constructed of a unitary, shaped flexible material. The central hub can also comprise a fixation aid, such as an adhesive configured to secure the plug to the surrounding tissue 80 in the airway wall. The fixation aid could, as illustrated in FIG. 17, comprise a plurality of anchors 262. According to some embodiments, the two-sided plug 260 can be configured to be inflated with a liquid, gas or any combination thereof. Such materials could include, for example, hydrogels, cyanoacrylates, tissue-based or fibrinogen glues, or other substances suitable for inflating the two-sided plug 260. Alternatively or additionally, the two-sided plug 260 could be constructed of compressible material and/or could be self-expanding upon withdrawal from a catheter (e.g., by using a resilient foam).

A method of implanting the two-sided plug 260 could include positioning the plug near a fistula 1 such that the two plug portions 261 are positioned on either side of the fistula 1. The two plug portions 261 then could self-expand and/or be inflated via an inflation member 17 in a working channel 108 of a delivery device 100. One or more of the plug portions 261 can include a valve or port configured to create selective fluid communication between the inflation member 17 and the interior of the plug portions 261. In some embodiments, the two-sided plug 260 is inflated in its entirety via the inflation member 17. Additionally, according to some embodiments, a plurality of anchors 262 on the central hub 263 can help hold the two-sided plug 260 in place in the vicinity of the fistula 1. In some embodiments, the two-sided plug 260 can be constructed of biocompatible materials and could be a permanent implant.

Figure 18A:
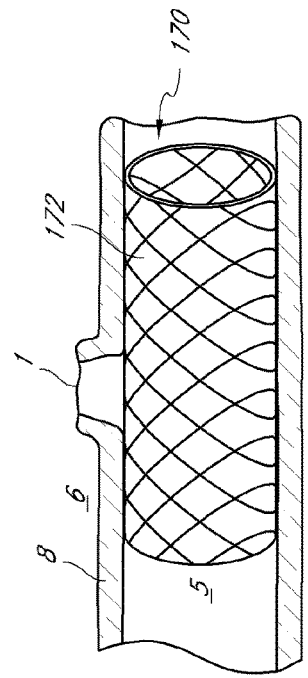
FIG. 18A is a perspective view of an embodiment of a woven-panel tube compressed within a catheter.
Figure 18B:
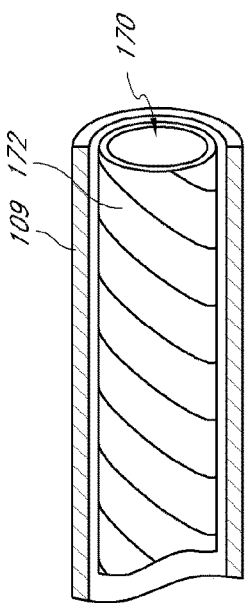
FIG. 18B is a perspective view of the woven-panel tube of FIG. 18A in an expanded configuration within a body lumen.

Hollow cylindrical devices can be used to treat fistulas that occur in the walls of airway passages 5. For example, as illustrated in FIGS. 18A-18B, a woven-panel tube 170 can be used to block a fistula 1 in the sidewall of an airway 5. The woven-panel tube 170 can comprise a plurality of panels 172. The panels 172 can be interwoven in a helical pattern such that, upon pulling of the ends of the woven-panel tube 170, the radius of the woven panel tube 170 decreases (e.g., like a Chinese finger trap). Additionally or alternatively, pushing on the ends of the woven-panel tube 170 (e.g., decreasing the length of the woven-panel tube) could increase the radius of the woven-panel tube 170. The panels 172 can be interwoven such that the tube 170 comprises a substantially-impermeable annular wall when the panels 172 are expanded into a body lumen.

In a preferred embodiment, the tube 170 is delivered to the site of the fistula 1 in a compressed state via a delivery catheter 109 within a working channel 108 of a delivery device 100, as illustrated in FIG. 18A. The tube 170 then is pushed from the delivery catheter 109 so that the tube 170 may expand radially within the airway 5. In some embodiments, the panels 172 bias the tube 170 into an expanded configuration. In some embodiments, a balloon is used to expand the tube 170 within an airway 5. In some configurations, radial expansion of the tube 170 seals the fistula 1. In some embodiments, the panels 172 are constructed of a material such as a resilient, impermeable polymer (e.g., polycarbonate, urethane, and/or polyester) that, when tightly-woven, provide a substantially impermeable interface.

Figure 19:
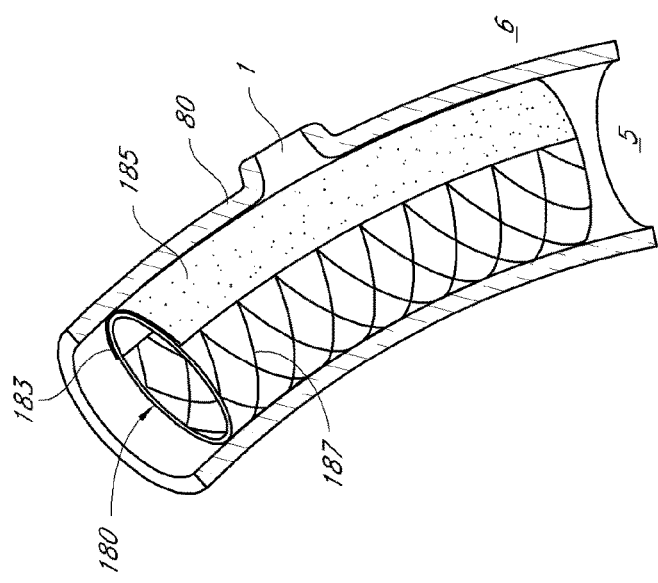
FIG. 19 is a perspective view of an embodiment of a partially-covered hollow cylinder deployed within a body lumen.

In certain case, a partially-covered hollow cylinder 180, as illustrated in FIG. 19, may be used to seal a sidewall fistula 1 in an airway 5. In some embodiments, a partially-covered hollow cylinder 180 comprises a plurality of structural members 187. The structural members 187 can be arranged in a helical, tubular configuration, creating a substantially cylindrical frame. According to some configurations, an arcuate segmental portion 183 of the outer surface of the cylindrical frame formed by the structural members 187 is covered with a covering 185 that comprises a substantially-impermeable material. In some embodiments, the partially-covered hollow cylinder 180 is delivered to the site of a side branch fistula 1 in a compressed state via a delivery catheter 109 in a working channel 108 of a delivery device 100. The partially-covered hollow cylinder 180 can be oriented in an airway 5 such that the substantially-impermeable covering 185 seals the sidewall fistula 1 and reduces the likelihood of the passage of fluid between the airway 5 and the surrounding cavity 6. In some embodiments, the covering 185 is located on the outside of the structural member 187. In some embodiments, the covering 185 is located on the inside of the structural members 187. The covering 185 can be attached to the structural members 187 before or after the structural members 187 are deployed to the site of the fistula 1.

In some embodiments, the uncovered portion of the hollow cylinder 180 allows for the passage of air and/or mucus along the airway wall 5 adjacent to the uncovered portions of the hollow cylinder 180. This passage of mucus can help keep other side branches from inadvertently being blocked. In some embodiments, the partially-covered hollow cylinder 180 can be constructed of biocompatible materials and could be a permanent implant. Additionally or alternatively, the covering 185 could comprise a mesh membrane that could be configured to block air passage after it has been implanted and becomes full of mucus. In some embodiments, the covering comprises a polymer, for example polycarbonate or urethane. In some embodiments, the plurality of structural members 187 comprise a material that can provide structural support for the partially-covered hollow cylinder 180. Such materials could include nitinol, polycarbonate, nylon, stainless steel, other suitable materials or any combination thereof.

Figure 20B:
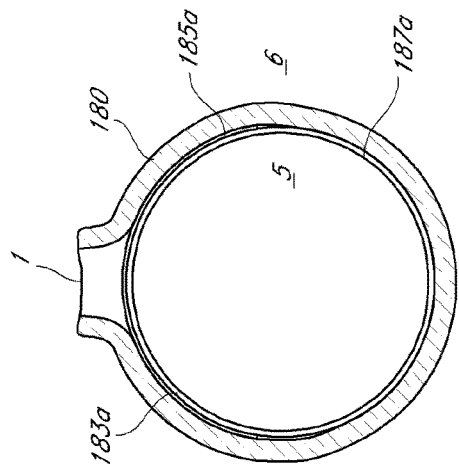
FIG. 20B is a front view of the partially-covered hollow cylinder of FIG. 20A.
Figure 20A:
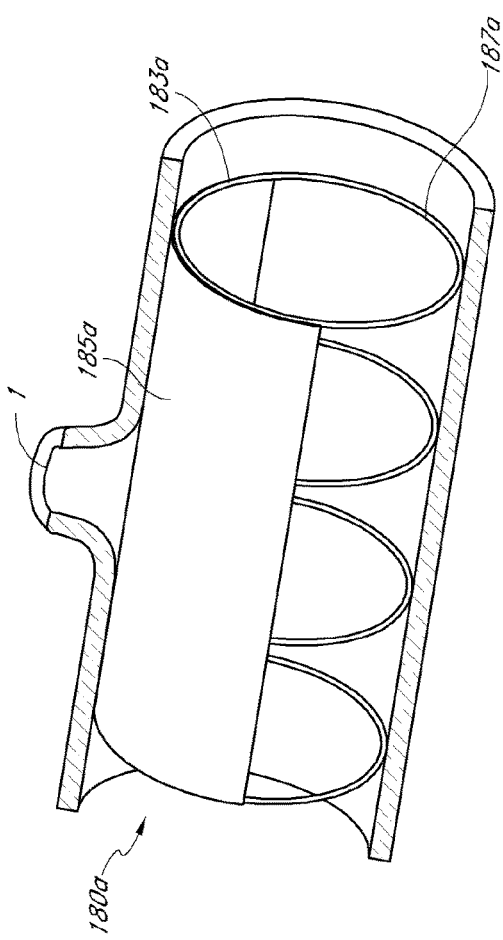
FIG. 20A is a perspective view of an embodiment of a partially-covered hollow cylinder deployed in a body lumen.
Figure 20C:
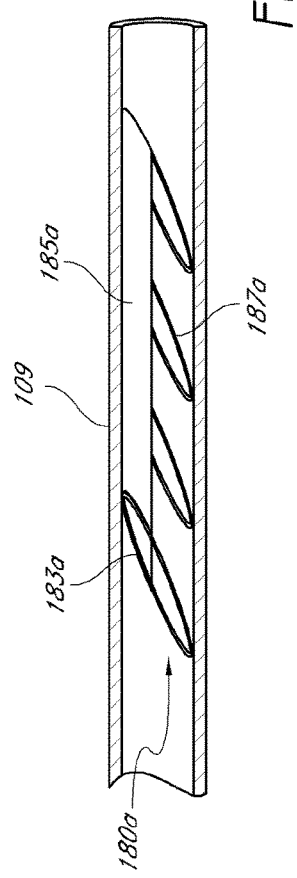
FIG. 20C is a perspective view of the partially-covered hollow cylinder of FIG. 20A compressed within a delivery catheter.

As illustrated in FIGS. 20A-20C, in some embodiments, the structural support for a partially-covered hollow cylinder 180a could be provided by a plurality of rings 187a. Like the structural members 187, the rings 187a could comprise metals (e.g., nitinol), or polymers (e.g., polycarbonate, nylon) and/or some other material that can provide sufficient structural support for the partially-covered hollow cylinder 180a. In some embodiments, the partially-covered hollow cylinder 180a could be delivered to the site of a side branch fistula 1 in a compressed state via a delivery catheter within a working channel 108 of a delivery device 100, as illustrated in FIG. 20C. Alternatively or additionally, structural support for a partially-covered hollow cylinder 185b could comprise a plurality of C-rings 187b, as illustrated in FIGS. 21A and 21B. In some embodiments, the plurality of C-rings 187b could comprise rounded or blunted portions 188. Additionally, according to some embodiments, support members for a partially-covered hollow cylinder 180c could be provided by a plurality of J-shaped rings 187c as illustrated in FIG. 22. In some embodiments, the plurality of J-shaped rings 187c could comprise atraumatic portions 188 that may be, for example, rounded or blunted.

Figure 23B:
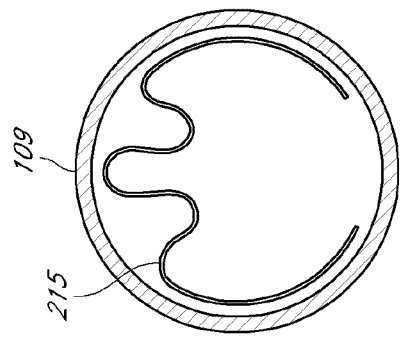
FIG. 23B is a front view of the ring device of FIG. 23A compressed within a delivery catheter.
Figure 23C:
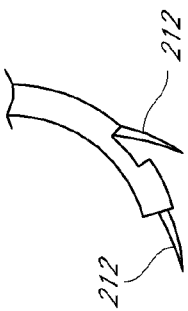
FIG. 23C is a close-up front view of the anchors of the ring device of FIG. 23A.
Figure 23A:
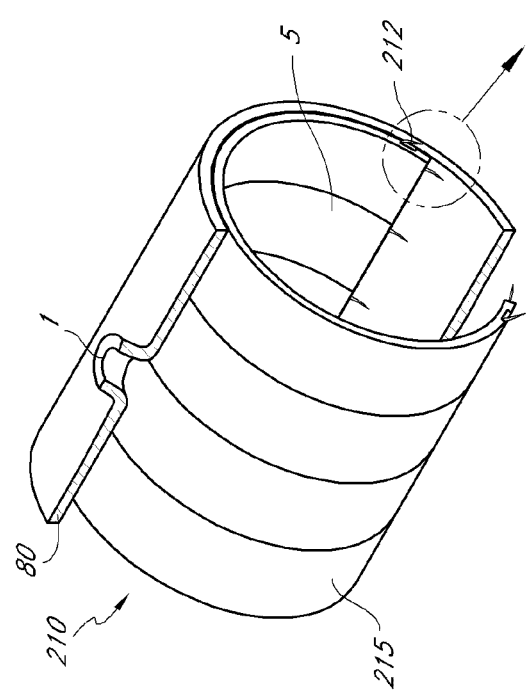
FIG. 23A is a perspective view of an embodiment of a ring device with anchors deployed in a body lumen.

In some variants, a method of treating a side-branch fistula 1 in an airway could comprise installation of a ring device 210, as illustrated in FIGS. 23A-23E. In some embodiments, a ring device 210 could comprise a plurality of rings 215. Preferably, the rings 215 would be constructed of a polymer material. According to some configurations, each of the rings 215 may comprise one or more anchors 212. In some embodiments, the ring device 210 could be delivered to the site of a sidewall fistula 1 in a compressed state via a delivery catheter 109 within a working channel 108 of a delivery device 100, as illustrated in FIG. 23B. Additionally or alternatively, according to some configurations the rings 215 can be constructed of memory shape material such that, upon removal from the delivery catheter 109, the ring device 210 could expand into the airway 5 on its own. Additionally or alternatively, a balloon could be inflated inside the ring device 210 after the ring device 210 is removed from the delivery catheter 109 in order to expand the ring device 210. The anchors 212 can engage with the tissue 80 of the airway 5 and hold the ring device 210 in place within the airway 5. The depth to which the anchors 212 engage with the tissue 80 of the airway 5 can be limited by pads and/or the outer surface of the rings 205. Additionally or alternatively, the ring device 210 could comprise a resilient material such that, when an airway 5 is collapsed (e.g., upon sneezing, hiccupping, coughing, etc.), the ring device 210 could conform to the collapsed geometry of the airway and could remained conformed to the airway 5 when the airway 5 recovers. This concept is illustrated in FIGS. 23D and 23E.

As illustrated in FIGS. 24A-24B, an X-frame plug 220 can comprise two or more support members 227, a central hub 212 and/or a plugging portion 220, wherein the support members 227 preferably intersect or join at the central hub 222. In some embodiments, the support members 227 can bias the plugging portion 220 of the X-frame plug 220 against the sidewall fistula 1. This biasing can help to seal the fistula 1 and reduce the likelihood of fluid communication between the airway 5 and the surrounding cavity 6.

A jellyfish plug 230, as illustrated in FIG. 25, could comprise a hemispherical covered portion 235 and a plurality of support members 237. The plurality of support members 237 are configured to form a substantially hemispherical frame upon which a covered portion 235 can be engaged. The plurality of support member 237 are further configured to comprise atraumatic ends 139 opposite the hemispherical covered portion 235. The atraumatic ends 139 could comprise loops, hooks, spherical portions or any other geometry configured to distribute pressure over an area larger than the cross section of the support members 237. The atraumatic ends 139 could, in some embodiments, be unitary with the support members 237. In some embodiments, the support members 237 of the jellyfish plug 230 could bias the covered portion 235 of the jellyfish plug 230 toward a fistula 1. This biasing can help to seal the fistula 1 and reduce the likelihood of fluid communication between the airway 5 and the surrounding cavity 6. In some embodiments, the jellyfish plug 230 could be used to treat side wall fistulas by placing the hemispherical covered portion 235 at the site of a side wall fistula 1 and allowing the support members 237 to bias the covered portion 235 of the plug 230 toward the fistula 1. In some embodiments, the jellyfish plug 230 could be used to treat stump leak geometries other than side wall fistulas.

As illustrated in FIGS. 26A-26B, a bench plug 240 could comprise a plug 245 and one or more support members 247. In some embodiments, the support members 247 can be configured to attach to the plug 245. The support members 247 are configured to expand away from the plug 245. The support members 247 can thus create radial force on the surrounding tissue 80 of the airway 5 or other body lumen and thereby bias the plug 245 of the bench plug 230 toward a sidewall fistula 1. This biasing can help to seal the fistula 1 and reduce the likelihood of fluid communication between the airway 5 and the surrounding cavity 6.

Figure 27:
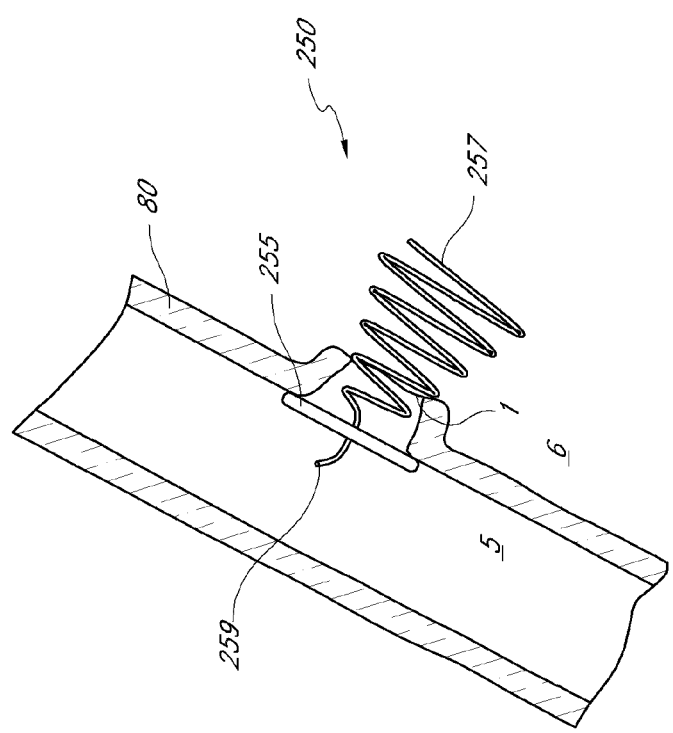
FIG. 27 is a side view of a plug deployed in a stump.

FIG. 27 illustrates an embodiment of a plug 250 that can be utilized to seal a sidewall fistula 1. In some embodiments, the plug 250 could comprise a plug member 255 and a biasing member 257. According to some embodiments, the biasing member 257 can be configured to pierce the plug member 255. The piercing end 259 could comprise one or more barbs that could inhibit the movement of the piercing end 259 back through the plug member 255 under normal stresses which occur in an airway 5. In some embodiments, the piercing end 259 could be constructed of high-friction material which could inhibit movement of the piercing end 259 with respect to the plug member 255. According to some embodiments, the biasing member 257 could be preloaded to expanded into the surrounding cavity 6 and thus create a pulling force on the piercing end 259 and the plug member 255. This pulling force could reduce the likelihood of the plug member 255 leaving the vicinity of the fistula 1.

It can be appreciated that portions of or entire embodiments of the above-described devices are preferably constructed from biocompatible materials so as to minimize any immune response or other reaction in the body tissue such devices may be implanted in. In some embodiments employing metals, for example, electropolishing of all or part of the device may be preferable to maximize biocompatibility, e.g., when using nitinol or stainless steel.

In some embodiments, the materials used may be configured to promote two- or three-dimensional growth of body tissue into or around the implanted device. For example, porous or spongy materials, for example porous PTFE, may be used in some embodiments. In an illustrative example, the central hub 143 of the conical valve 140 illustrated in FIGS. 10A-10B could be constructed of a material such as porous PTFE. The material of the central hub 143 may thus facilitate the growth of tissue 80 surrounding the conical valve 140 into the central hub 143. In this way, the conical valve 140 could be implanted for a long term treatment or permanently. Other porous materials, including foams, ceramics, and metals (e.g., porous titanium) may be used as well. In some embodiments, the porous material may be derived from animal or cadaveric tissue, or made from proteins found in tissue (e.g., collagen, fibrin, elastin, chitosan).

In some embodiments, it may be advantageous to use a bioresorbable or bioabsorbable material in the construction of all or part of the device to be implanted. Such materials are typically either broken down or absorbed by the body over a period of time (e.g., via hydrolysis), and the time necessary for resorption may be tailored by selecting an appropriate material and/or processing conditions. Some preferable materials include polymers such as polylactides, polyglycolides, poly-caprolactones, polydioxanones, polyamino acids (e.g., polylysines, polyglutamates, polyleucines), and proteins (including structural proteins such as collagen, fibrin, elastin, chitosan). Various copolymers of the preceding examples are also envisioned.

Additionally or alternatively, all or a portion of the above-described devices may be coated with compounds that have properties that enhance biocompatibility. For example, compounds may be selected that promote tissue growth, reduce or promote inflammation, promote vascularization, reduce or inhibit bacterial growth, and so forth. In some embodiments, and in particular when using porous materials, all or part of the device may also or additionally be seeded with cells. For example, stem cells, fibroblasts, and/or chondrocytes may be cultured or provided in conjunction with the devices described herein.

Although certain embodiments and examples have been described herein, it will be understood by those skilled in the art that many aspects of the methods and devices shown and described in the present disclosure may be differently combined and/or modified to form still further embodiments. Additionally, it will be recognized that the methods described herein may be practiced using any device suitable for performing the recited steps. Such alternative embodiments and/or uses of the methods and devices described above and the obvious modifications and equivalents thereof are intended to be within the scope of the present disclosure.

What is claimed is:

1. A device for treating fistulas in walls of a body cavity or lumen, the device configured to transition between a compressed and an expanded configuration, the device further configured to fit within a working channel of an endoscope with the device is in a compressed configuration, the device comprising:
    a first conical portion and a second conical portion, the conical portions configured to transition between a compressed and an expanded configuration, the conical portions configured to restrict the flow of fluid through a fistula in at least one direction when the conical portions are in an expanded configuration and deployed at the site of a fistula; and
    a rod comprising a first end and a second end,
    wherein the first conical portion comprises:
        a first end connected to the first end of the rod; and
        a second end configured to form a contiguous cone opening when in the expanded configuration,
    wherein in the second conical portion comprises:
        a first end connected to the rod between the first end of the rod and the second end of the rod; and
        a second end configured to form a contiguous cone opening when in the expanded configuration,
    wherein the cone opening of the first conical portion has a greater diameter than the cone opening of the second conical portion,
    wherein the first end of the second conical portion is located closer to the first end of the rod than the second end of the second conical portion,
    wherein the first and second cones comprise a flexible membrane configured to restrict airflow through the fistula,
    wherein one or more of the first ends of the conical portions are slidably connected to the rod.

2. The device of claim 1, wherein at least one of the conical portions are configured to expand to the radius of a body lumen when the device is deployed within a body lumen.

3. The device of claim 1, wherein the cone openings of the first and second conical portions face the second end of the rod.

4. The device of claim 3, wherein a portion of the cone opening of the second conical portion is located within the cone opening of the first conical portion after one of the first ends of the conical portions has been slid along the rod toward the first end of the other conical portion.

* * * * *